(12) United States Patent
Kapur

(10) Patent No.: US 11,547,786 B2
(45) Date of Patent: Jan. 10, 2023

(54) EXPANDABLE ECMO EXTENSION CANNULA SYSTEM

(71) Applicant: Tufts Medical Center, Inc., Boston, MA (US)

(72) Inventor: Navin K. Kapur, Hanover, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 17/663,205

(22) Filed: May 12, 2022

(65) Prior Publication Data

US 2022/0280709 A1 Sep. 8, 2022

Related U.S. Application Data

(63) Continuation-in-part of application No. PCT/US2021/025461, filed on Apr. 1, 2021, which is a continuation-in-part of application No. 16/840,284, filed on Apr. 3, 2020, now Pat. No. 11,331,421.

(51) Int. Cl.
*A61M 1/36* (2006.01)
*A61M 1/16* (2006.01)
*A61M 25/00* (2006.01)
*A61M 39/10* (2006.01)

(52) U.S. Cl.
CPC ........ *A61M 1/3659* (2014.02); *A61M 1/1698* (2013.01); *A61M 25/0054* (2013.01); *A61M 39/10* (2013.01); *A61M 2025/0057* (2013.01)

(58) Field of Classification Search
CPC .............. A61M 1/3659; A61M 1/3613; A61M 25/0012; A61M 39/06; A61M 2025/0024; A61M 2210/127; A61M 2039/0633

See application file for complete search history.

(56) References Cited

U.S. PATENT DOCUMENTS

| 5,125,903 A | 6/1992 | McLaughlin et al. |
| 5,195,980 A | 3/1993 | Catlin |
| 5,269,764 A | 12/1993 | Vetter et al. |
| 6,083,198 A | 7/2000 | Afzal |

(Continued)

OTHER PUBLICATIONS

International Search Report & Written Opinion dated Sep. 13, 2021 in Int'l PCT Patent Appl. Serial No. PCT/US2021/025461 (0510).

(Continued)

*Primary Examiner* — Emily L Schmidt
(74) *Attorney, Agent, or Firm* — Eversheds Sutherland (US) LLP; Nicola A. Pisano; Albert K. Heng

(57) ABSTRACT

An extension cannula and in-line connector for use with a conventional ECMO return cannula is provided. The extension cannula includes a flexible conduit transitionable between a collapsed insertion state and an expanded deployed state when in communication with blow flow from an ECMO machine via the ECMO return cannula. The extension cannula may be positioned through a conventional ECMO return cannula such that the proximal end of the flexible conduit is disposed within and proximal to the end of the ECMO return cannula, while the distal end of the flexible conduit is disposed in a patient's thoracic aorta to deliver oxygenated blood directly to the patient's thoracic aorta via one or more pores at the distal region of the flexible conduit to improve cerebral oxygenation, maintain systemic arterial pulsatility, and reduce the potential for end-organ injury.

30 Claims, 31 Drawing Sheets

(56) References Cited

U.S. PATENT DOCUMENTS

| | | |
|---|---|---|
| 6,183,443 B1 | 2/2001 | Kratoska et al. |
| 6,210,365 B1 | 4/2001 | Afzal |
| 6,241,666 B1 | 6/2001 | Pomeranz et al. |
| 6,632,236 B2 | 10/2003 | Hogendijk |
| 7,938,809 B2 | 5/2011 | Lampropoulos et al. |
| 8,996,095 B2 | 3/2015 | Anderson et al. |
| 9,144,662 B2 | 9/2015 | Di Caprio et al. |
| 10,485,956 B2 | 11/2019 | O'Donovan |
| 2006/0079859 A1 | 4/2006 | Elkins et al. |
| 2013/0274783 A1 | 10/2013 | Wynberg |
| 2014/0012281 A1 | 1/2014 | Wang et al. |
| 2014/0221964 A1 | 8/2014 | Xiao et al. |
| 2016/0158489 A1 | 6/2016 | Wu et al. |
| 2017/0080178 A1 | 3/2017 | O'Connell et al. |
| 2017/0238951 A1 | 8/2017 | Yang et al. |
| 2018/0193026 A1 | 7/2018 | Yang et al. |
| 2018/0207399 A1 | 7/2018 | Chou et al. |
| 2018/0243004 A1 | 8/2018 | Von Segesser |
| 2019/0160259 A1 | 5/2019 | Cottone et al. |
| 2019/0247564 A1 | 8/2019 | Lu et al. |
| 2019/0358434 A1 | 11/2019 | Fuller et al. |
| 2020/0146852 A1 | 5/2020 | Raychev et al. |
| 2021/0308359 A1 | 10/2021 | Kapur |

OTHER PUBLICATIONS

Pavlushkov, et al., Cannulation Techniques for Extracorporeal life Support, Review Article on Extracorporeal Life Support, Annals of Translational Medicine, 5(4):70 (Feb. 2017).

Sulimov, M.D., et al., Rescue Peripheral Intervention Using A Peripheral ECMO-Cannula as Vascular Access, J. Amm. Golf. Cardial. Intv., Jan. 29, 2020, epublished 001:10.1016/j.jcin.2019.11.038.

Swain, et al., Transvalvular Ventricular Unloading Before Reperfusion in Acute Myocardial Infarction, Journal of the American College of Cardiology, 76(6):685-699 (Aug. 2020).

EXPANDABLE ECMO EXTENSION CANNULA SYSTEM

CROSS-REFERENCE TO RELATED APPLICATIONS

This application is a continuation-in-part application of International PCT Patent Application Serial No. PCT/US2021/025461, filed Apr. 1 2021, which is a continuation-in-part application of U.S. patent application Ser. No. 16/840,284, filed Apr. 3, 2020, now U.S. Pat. No. 11,331,421, the entire contents of each of which are incorporated herein by reference.

FIELD OF THE INVENTION

This application relates generally to systems and methods for improving systemic perfusion and reducing complications during venous-arterial extracorporeal membrane oxygenation (VA-ECMO), and more specifically, for improving perfusion using an in-line connector and an extension cannula to deliver oxygenated blood directly to the thoracic aorta.

BACKGROUND

Nearly 23 million people suffer from heart failure (HF) worldwide, which affects approximately 7 million individuals in the United States with healthcare expenditures reaching nearly 40 billion dollars per year. Acute myocardial infarction (AMI) is a leading cause of HF and occurs in over 650,000 individuals per year in the United States. Despite early revascularization in AMI, for every 5% increase in infarct size, one-year mortality and HF hospitalization are increased by 20%. Paradoxically, coronary reperfusion may accelerate myocardial injury and cardiomyocyte death in AMI. Despite improvements in reperfusion time, subsequent HF remains a significant problem and new approaches are needed to reduce myocardial damage in AMI.

Arterial perfusion to every major organ system, including the heart, kidneys and brain, is determined by arterial pressure, blood flow, vascular tone, and intra-organ vascular resistance. When a patient experiences low arterial perfusion due to heart failure, cardiopulmonary failure, and cardiogenic or septic shock, venous-arterial extracorporeal membrane oxygenation (VA-ECMO) systems may be used to provide both circulatory and gas exchange support by augmenting the flow of oxygenated blood. See, e.g., Pavlushkov E, Berman M, Valchanov K. Cannulation techniques for extracorporeal life support. Ann Transl Med 2017; 5(4):70. doi: 10.21037/atm.2016.11.47. Specifically, VA-ECMO drains blood from the venous system, oxygenates this blood outside of the patient, and then delivers oxygenated blood back to the arterial system, e.g., via the femoral artery. VA-ECMO is most commonly performed via large-bore cannulas placed in the femoral vein and femoral artery (known as peripheral VA-ECMO). VA-ECMO is an established strategy for cardiopulmonary support. Large-bore ECMO cannulae for use in adult humans generally range in diameter from 15 Fr (5.0 mm) to 25 Fr (8.3 mm) and are used to deliver life-sustaining blood flow rates of between 3 and 8 liter/min.

Despite increasing utilization of VA-ECMO, with nearly 5,000 extracorporeal membrane oxygenation devices in use annually in the U.S. alone, in-hospital mortality remains around 60%. One explanation for these poor outcomes is that peripherally cannulated VA-ECMO may cause kidney injury, increase the risk of stroke, and promote cerebral ischemia, bleeding, and vascular injury. Further, more than one large-bore cannula may be required to achieve high flow rates needed for systemic perfusion with VA-ECMO. Cannula number and size are directly associated with increased risk of bleeding, vascular trauma, and acute limb ischemia. Finally, peripherally cannulated VA-ECMO may pressurize the entire aorta and increase pressure inside the heart, which increases ventricular wall stress and myocardial oxygen consumption, thereby expanding myocardial damage or infarct size in the setting of a heart attack and increasing fluid in the lungs thereby causing acute lung injury. Recent data also shows that VA-ECMO may cause damage to mitochondria located within the heart, which may limit myocardial recovery. To mitigate heart or lung injury, concomitant devices such as intra-aortic balloon pumps and Impella® pumps (made available by AbioMed, Danvers, Mass.) may be used concomitantly with VA-ECMO and require additional vascular puncture. All of these complications are associated with increased mortality, long-term morbidity, length of stay in the hospital, and healthcare costs. New approaches to limit complications associated with VA-ECMO are required.

Studies indicate that VA-ECMO support may decrease kidney function and even cause acute kidney injury due to increased arterial pressure and loss of pulsatile flow to the kidney resulting from the high rates of blood flow localized to the outlet region of arterial outlet return cannulas with conventional VA-ECMO. Such injuries may in turn activate autoregulatory mechanisms of the kidneys. For example, high rates of non-pulsatile flow encountered with conventional VA-ECMO cannulas have been observed to increase vascular resistance, which in turn increases the workload of the kidneys and exacerbates oxygen consumption. Up to 70% of patients receiving VA-ECMO develop acute kidney injury, which is directly associated with mortality. Studies have further indicated that use of VA-Emay lead to a significant increase in arterial flow, as well as promote an increase in pressure within the organ itself, which in turn decreases flow in the renal vein. Thus, the net effect of VA-ECMO use, with conventional return cannulas, is an increase in pressure inside the organ, such that flow through the kidney is decreased. These physiological findings correlate with an increase in biomarkers of kidney injury, suggesting that one mechanism responsible for kidney injury may be related to pressure build-up inside the kidney and a net decrease of blood flow through the kidney.

Previously known efforts to reduce perfusion injury are known in the art. For example, U.S. Pat. No. 6,083,198 to Afzal describes a perfusion catheter having segmented flow regions, in which an arterial return catheter includes a series of apertures along its length to more evenly distribute blood within the aorta, including the aortic arch. One drawback of the system described in that patent, however, is that the inner catheter includes a reduced diameter than the outer catheter, thereby reducing flow rates to the distal-most portions of the catheter.

Recent studies also indicate that VA-ECMO use results in increased risk of stroke, e.g., acute ischemic stroke and hemorrhagic stroke. Because VA-ECMO induces retrograde blood flow in the femoral artery towards the aorta, the brain is the last major organ to receive oxygenated blood delivered via a conventional femoral artery cannula. Further, in patients exhibiting north-south syndrome, e.g., when compromised lung function results in ejection of deoxygenated blood from the left ventricle into the ascending aorta, differential hypoxia may occur as a result of VA-ECMO patients' dependence on retrograde flow to deliver oxygenated blood to the upper body. To mitigate this effect, physicians currently perform additional vascular punctures in the arteries or veins to place additional large-bore cannulas that increase the risk of complications.

Central VA-ECMO, in which oxygenated blood is delivered directly to a central location, e.g., via a surgical cut-down to the aortic arch, has been hypothesized to provide more oxygenated blood flow to the brain and thus reduce the risk of stroke. However, such cannulation, as described for example in U.S. Pat. No. 6,210,365 to Afzal, requires invasive surgery and involves additional potential complications. Another solution theorized would be to deliver oxygenated blood directly to the venous side of the patient via an ECMO cannula; however, this would require creating additional large-bore punctures in the patient's vasculature and may be further complicated by the already existing cannula residing in the venous circulation from the original VA-ECMO configuration. Additionally, placement of rigid cannulas from the peripheral artery into a central location in the thoracic aorta may be limited by the inability to navigate large bore cannulas through the iliofemoral bifurcation, tortuous aortas, or across calcified aortas with atheromatous material lining the aorta.

In view of the foregoing, it would be desirable to provide systems and methods for delivering oxygenated blood via VA-ECMO from a point of entry in the femoral artery to a more central location to the patient, e.g., the thoracic aorta, to supply oxygenated blood to the brain and induce antegrade flow to lower portions of the descending aorta. Such systems and methods may thus improve blood flow to the brain, preserve brain function, reduce the risk of ischemic stroke, and reduce blood flow rates and pressures that could induce kidney injury.

U.S. Pat. No. 8,996,095 to Anderson describes a coronary guide extension catheter having a push member and a distal tubular member, which is configured to be positioned in a coronary artery for use during percutaneous transluminal coronary angioplasty. The guide extension catheter described in that patent is designed to stabilize the distal end of a coronary guide catheter to prevent movement away from the patient's ostium due to beating of the heart during the interventional procedure. Similarly, U.S. Pat. No. 10,485,956 to O'Donovan describes a guide extension catheter having a groove in a push member and a distal shaft for guiding an interventional coronary device therethrough. Such coronary guide extension catheters are unsuitable for use as perfusion cannulas in VA-ECMO due to the small lumen diameters and resulting low blood flow rates that could be achieved. Guide extension catheters typically have a fixed diameter of between 6 Fr (2 mm) and 8 Fr (2.7 mm). These coronary guide extension catheters are not meant to redirect blood flow, but rather to facilitate delivery of coronary equipment into distal portions of the coronary vasculature.

U.S. Pat. No. 6,632,236 to Hogendijk describes a self-expanding catheter for use in stent delivery, in which a catheter is transluminally inserted in a collapsed delivery state, and self-expands to an expanded deployed state upon removal of a delivery sheath. That patent describes a self-expanding anchor formed of a self-expanding wire weave having an elastomeric polymeric coating, and is configured to protect against embolization during vascular interventions. The concept described in Hogendijk is not meant to redirect blood flow, but rather to filter out elements in the blood stream. Similarly, U.S. Pat. No. 6,183,443 to Kratoska describes an expandable introducer sheath for percutaneously introducing intravascular angioplasty catheters. Such self-expanding catheters have not been contemplated for use with VA-ECMO systems for perfusing oxygenated blood.

In view of the disadvantages of the previously known ECMO perfusion catheters, it would be desirable to provide a device for use with an ECMO system that can enhance blood flow to the thoracic aorta and aortic arch, improve cerebral oxygenation, maintain systemic arterial pulsatility, and reduce the potential for perfusion injury to the kidneys using a single port of access, thereby avoiding bleeding and vascular injury associated with contemporary VA-ECMO.

It further would be desirable to provide a device for use with an ECMO system that avoids the small flow lumen sizes of previously known reperfusion catheters, thereby permitting enhanced blood flow rates to the ascending aorta and aortic arch, while maintaining or reducing the diameter of the vascular opening to the femoral artery required to introduce the return cannula.

In contemporary practice, VA-ECMO is also used to support commonly performed life-saving procedures such as coronary angioplasty, aortic valvuloplasty, or aortic valve replacement. However, a major limitation of these approaches is the need for additional vascular access to place vascular sheaths and/or catheters for required interventional equipment in addition to the existing VA-ECMO circuit. This can be prohibitive for patients who have peripheral vascular disease, concomitant vascular injury, or vessels occupied by other life-saving equipment. Further, under emergent conditions, placing additional vascular access can be challenging and increase risk of injury.

U.S. Pat. Nos. 5,125,903, 5,195,980, 5,269,764, 7,938,809 describe percutaneous catheter introducers/connectors having hemostatic valves for permitting passage of elongated interventional devices into a patient's vasculature, and a side port for connection with, e.g., an outside source of perfusion, aspiration, contrast media, medicaments, etc. These systems are not designed for use with VA-ECMO. Moreover, no existing approach allows for simple and effective access to the VA-ECMO circuit for delivery of additional interventional equipment. Current Y-connectors used to provide access to an ECMO circuit suffer from numerous disadvantages including reduction in the effective lumen of the ECMO return cannula creating an undesirable pressure gradient, difficult angulations requirements that prohibit introduction of additional catheters without risk of kinking or catheter disruption. Such previously known connectors require the introducer sheath to be inserted nearly 25 to 30 cm more distal than usual due to interposition connecting tubing, thereby limiting access to the thoracic aorta, aortic root, aortic valve or coronary vasculature for therapeutic interventions. Such connectors also pose a risk of bleeding during ECMO disconnection and reconnection, with increased risk of air embolism and contamination due to disconnection from the ECMO circuit. See, e.g., Dmitriy S. Sulimov, M D et al., "Rescue Peripheral Intervention Using a Peripheral ECMO-Cannula as Vascular Access," J Am Coll Cardiol Intv. 2020 Jan. 29. Epublished DOI: 10.1016/j.jcin.2019.11.038.

It would therefore be desirable to provide a connector for providing simple and effective access to an ECMO circuit for delivery of interventional equipment.

SUMMARY OF THE INVENTION

In accordance with the principles of the present invention, devices and methods are provided for use with ECMO systems that overcome the disadvantages of the previously known ECMO reperfusion catheters. Specifically, devices constructed in accordance with the present invention enhance blood flow to the thoracic aorta, improve cerebral oxygenation, maintain systemic arterial pulsatility, and reduce the potential for end-organ injury.

In accordance with one aspect of the present invention, an extension cannula for use with an ECMO return cannula that defines a blood flow path is provided. The extension cannula may include the ECMO return cannula, an elongated shaft, e.g., a hypotube, and a flexible sock-like conduit coupled to the distal region of the elongated shaft. The flexible conduit may be formed of a biocompatible fabric, e.g., at least one of polyethylene, polyurethane, or nylon, and the distal region of the flexible conduit may include a plurality of pores to permit blood flow to exit therethrough. The proximal end of the flexible conduit may engage with the outlet of the ECMO return cannula to form a continuation of the blood flow path through the lumen of the ECMO return cannula, such that the flexible conduit may transition between a collapsed insertion state and an expanded deployed state when in communication with a blood flow from the ECMO machine through the internal lumen of the flexible conduit. Preferably, the proximal end of the flexible conduit may be incorporated into the conventional ECMO return cannula as a single built unit, such that the extension cannula including the flexible conduit and the ECMO return cannula may be advanced into the patient as a single unit, without the need for an existing ECMO return cannula disposed in the patient. Alternatively, in some embodiments, the proximal end of the flexible conduit may be removably coupled to a conventional ECMO return cannula, e.g., via an expandable anchor as described in further detail below, such that the flexible conduit may be advanced through an ECMO return cannula disposed in the patient in a collapsed delivery state, and expanded within the patient.

The extension cannula further may include a connection structure, e.g., one or more umbrella-like struts, that couples the flexible conduit to the distal region of the elongated shaft. The elongated shaft may be used to advance the flexible conduit to locate the distal end beyond the patient's renal vessels, and the flexible conduit may have a length selected so that when the extension cannula is in the expanded deployed state, the proximal end is located within the outlet of the ECMO return cannula at a location proximal of the patient's renal vessels, and the distal end extends beyond the outlet of the ECMO return cannula and the patient's renal vessels.

The elongated shaft may have a length selected so that the elongated shaft extends proximally from the tip through the internal lumen of the flexible conduit and beyond the proximal end of the flexible conduit. In addition, the lumen of the elongated shaft may be sized and shaped to receive a guidewire therethrough. Moreover, the extension cannula may include an in-line connector coupled between the ECMO machine and the ECMO return cannula, and the in-line connector may include a side arm with a lumen in fluid communication with the lumen of the elongated shaft. Accordingly, the extension cannula may be advanced over a guidewire to the target location within the patient's vasculature by advancing the elongated shaft over the guidewire until the proximal end of the guidewire extends out of the side arm. The in-line connector may be removably coupled to the conventional ECMO return cannula, or it may be incorporated into the conventional ECMO return cannula as a single unit.

A stylet may be inserted into the lumens of the side arm of the in-line connector and the elongated shaft to prevent blood flow therethrough during operation of the ECMO machine.

The proximal end of the flexible conduit may engage with the outlet of the ECMO return cannula by an anchoring stent. For example, the anchoring stent may be self-expandable. Accordingly, a sheath may be removably disposed over the flexible conduit to retain the flexible conduit in the collapsed insertion state, such that upon retraction of the sheath, the flexible conduit is exposed within the patient's vasculature. In some embodiments, the proximal region of the flexible conduit may be fixedly coupled to the ECMO return cannula within the outlet of the ECMO return cannula.

In some embodiments, the extension cannula further may include an in-line connector separate from the ECMO return cannula. The in-line connector may have a first branch sized and shaped to be removably coupled to an outlet of an ECMO circuit, a second branch having a lumen sized and shaped to permit insertion of the extension cannula therethrough, and an outlet sized and shaped to be removably coupled to the ECMO return cannula, such that the first and second branches are in fluid communication with the outlet of the in-line connector. In addition, the second branch may be co-linear with the outlet of the in-line connector. The in-line connector may be removably coupled to the conventional ECMO return cannula, or it may be incorporated into the conventional ECMO return cannula as a single unit.

In accordance with another aspect of the present invention, a cannula for use with an ECMO machine is provided. The cannula may include a proximal region having an inlet sized and shaped to be coupled to an ECMO machine, and an outlet sized and shaped to be disposed at a location within a patient's vasculature proximal of a patient's renal vessels. For example, the cannula may include a conduit formed by a flexible and collapsible tube having a proximal end, a distal end, a length extending therebetween, and a lumen in an expanded deployed state. The conduit may transition from a collapsed insertion state to the expanded deployed state when in communication with a blood flow from the ECMO machine. The cannula further may include an elongated shaft having a distal region coupled to the distal end of the conduit, such that the elongated shaft may be used to advance the conduit in the collapsed insertion state to locate the distal end beyond the patient's renal vessels. Moreover, the length of the conduit may be selected so that when the proximal end is located within the outlet at the location within the patient's vasculature proximal of the patient's renal vessels, the distal end extends beyond the patient's renal vessels, and the conduit transitions to the expanded deployed state in the presence of blood flow from the ECMO machine so that the lumen forms a continuation of a blood flow path through the cannula. The flexible conduit may include a distal region having a multiplicity of pores sized and shaped to permit the blood flow to exit the lumen. In addition, the proximal end of the conduit may be affixed to the outlet by a stent.

In accordance with yet another aspect of the present invention, an extension cannula for use with a conventional ECMO return cannula is provided. The extension cannula includes an elongated shaft having a proximal end and a distal region, and a conduit coupled to the distal region of the elongated shaft. The elongated shaft may be used to position a proximal end in fluid communication with the lumen of the conventional ECMO return cannula, so that a distal end of conduit extends beyond the renal arteries, e.g., within the thoracic or abdominal aorta. The shaft may include a proximal end that extends through a port near a proximal end of the ECMO return cannula, where it may be manipulated by the clinician. The conduit has an inlet, an outlet, an internal lumen extending therebetween, and a diameter configured to transition between a collapsed insertion state and an expanded deployed state. The internal diameter of the conduit may be sized and shaped to receive at least one of a catheter for coronary, peripheral vascular, cerebral intervention, or valve intervention, a catheter for antegrade limb perfusion, or a catheter for delivery of intra-aortic, trans-valvular pneumatic, or rotary flow pumps.

In a preferred embodiment, the conduit has a length selected so that when the extension cannula is inserted through a lumen of the conventional ECMO return cannula, the inlet of the conduit is in fluid communication with the outlet of the conventional ECMO return cannula and the outlet of the conduit extends beyond the renal arteries, and may reside in a patient's thoracic aorta, e.g., the descending aorta, the aortic arch, or the ascending aorta. In accordance with the principles of the present invention, as used herein, the patient's thoracic aorta may include the portion of the descending aorta above the level of the diaphragm such that the outlet of the conduit may reside in the descending aorta approaching the level of the diaphragm from beneath the patient's thoracic cavity. The conduit may include a support structure, such as a self-expanding mesh, weave or braid, encapsulated with a flexible biocompatible coating, e.g., ePTFE. Alternatively, the support structure may include a shape-memory alloy, plastic or stainless steel spine or skeleton. As a further alternative, the conduit may be take the form of a hollow sock-like structure having one or more pores coupled to a flexible spine or hypotube. For example, the plurality of pores may be disposed in a lateral surface of the conduit. In this latter embodiment, the sock-like structure expands when filled with blood being ejected from the ECMO circuit. For example, the conduit may be formed of a soft, flexible material such that it may transition to the deployed state by blood pumped by the ECMO system through the internal lumen. The plurality of pores of the soft, flexible material allows blood to exit the lumen without jetting.

The extension cannula of present invention is expected to provide improved delivery of oxygenated blood from the ECMO machine. For example, the conduit may have a length selected, e.g., 20-80 cm, so that when the extension cannula is inserted through the lumen of the ECMO return cannula and transitioned to the expanded deployed state, e.g., in the presence of blood flow from the ECMO machine, the inlet of the conduit may be in fluid communication with the outlet of the ECMO return cannula, the outlet of the conduit may extend beyond the patient's renal vessels, e.g., into the aortic arch, and the internal lumen may form a continuation of the blood flow path through the internal lumen to deliver blood flow from the ECMO machine beyond the patient's renal vessels, e.g., to the patient's aortic arch, to thereby reduce cardiac workload of the patient's right and left ventricles. Moreover, the reduction of cardiac workload may reduce left ventricular injury and reduce long-term effects of cardiac infarct.

In accordance with yet another aspect of the present invention, the single built ECMO cannula may be configured to be positioned through a femoral vein, with the inlet of the extension cannula disposed within a patient's pulmonary artery, thereby serving as a cannula that selectively enables blood to be withdrawn from the pulmonary artery into the ECMO circuit. With this approach, it may be possible to reduce flow across the lung, thereby reducing left ventricle wall stress and distention, by decreasing preload to the left ventricle.

As a yet further alternative, the outlet of the single built extension cannula may be disposed in a patient's aortic root or left ventricle, and may be dimensioned to receive at least one of a catheter for coronary, peripheral, cerebral vascular or valvular interventions, or for placement of additional pump technologies within the left ventricle, such as a pneumatic or rotary flow pump inside the aorta, e.g., an intra-aortic balloon pump (IABPs), or trans-valvular rotary flow pump, e.g., Impella® pumps (made available by AbioMed, Danvers, Mass.).

In accordance with still another aspect of the invention, a single built extension cannula for use with an ECMO inlet cannula is provided having an inlet and an outlet. The extension cannula includes an elongated shaft having a proximal end and a distal region, and an expandable conduit coupled to the distal region of the elongated shaft. The conduit has an inlet, an outlet and an internal lumen, and has a diameter that transitions between a collapsed insertion state and an expanded deployed state. The conduit has a length selected so that when the extension cannula is inserted through a lumen of the ECMO inlet cannula, the outlet of the conduit is in fluid communication with the outlet of the ECMO inlet cannula and the inlet of the conduit resides in a patient's right ventricle.

Methods of using the extension cannula of the present invention also are provided. For example, the extension cannula of the present invention may be used for reducing or preventing myocardial damage in a subject caused by acute myocardial infarction, heart failure, cardiac arrest, pulmonary embolism, myocarditis, or lung injury, e.g., by reducing left heart workload and improving function of mitochondrial CI. In addition, the extension cannula of the present invention may be used for reducing myocardial infarct size due to an obstruction of coronary blood flow and limiting the development of post-infarction heart failure. Moreover, the extension cannula of the present invention may be used for increasing cardio-protective signaling pathways in the heart during acute myocardial infarction or heart failure to reduce myocardial injury and improve myocardial recovery, ameliorating the effects of compromised lung function and reducing the occurrence and severity of north-south syndrome, and enhancing antegrade blood flow to the patient's descending aorta and adjoining arteries, thereby unloading the patient's left ventricle, reducing cardiac output at a lower pressure, and decreasing left and right ventricular workload.

DETAILED DESCRIPTION OF THE INVENTION

Systems and methods are provided for use with ECMO systems to enhance blood flow to the thoracic aorta, ascending aorta and aortic arch, thereby facilitating normal antegrade flow to the carotid and other downstream arteries, while reducing high blood flow rates and the potential for reperfusion injury to the kidneys. The systems and methods of the present invention also may ameliorate the occurrence of north-south syndrome in patients with impaired lung function, thereby ensuring adequate flow of oxygenated blood to the patient's cerebral vasculature.

Figure 1A:
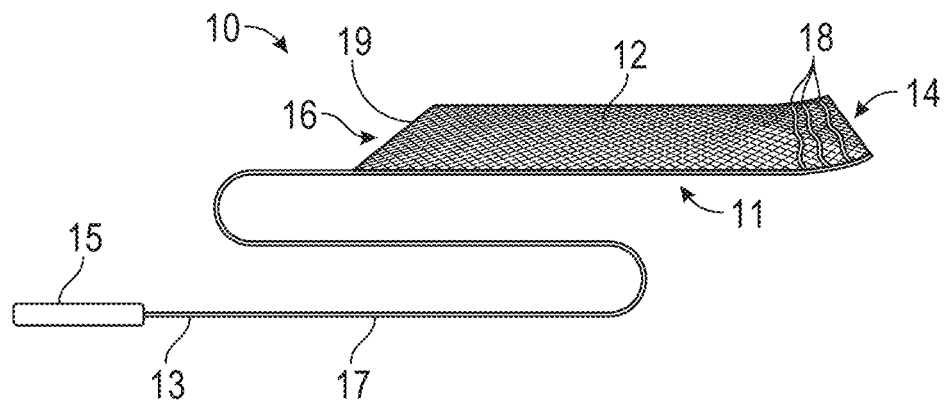
FIG. 1A is a side view of an extension cannula for improving reperfusion during ECMO, constructed in accordance with the principles of the present invention, with the extension conduit in an expanded state and with the delivery sheath removed.

Referring to FIG. 1A, extension cannula 10 suitable for use with a conventional VA-ECMO cannula is described. Extension cannula 10 includes shaft 17 extending between distal region 11 and proximal region 13 of extension cannula 10. Shaft 17 is formed of a material, e.g., stainless steel rod, having sufficient rigidity to permit cannula 10 to be advanced through a conventional ECMO reperfusion cannula so that distal region 11 of self-expanding conduit 12 may be disposed with its outlet extending beyond a patient's renal arteries, and preferably extending in a patient's ascending aorta or in the vicinity of the aortic arch. Self-expanding conduit 12 optionally may include handle 15 coupled to shaft 17 at proximal region 13 of self-expanding conduit 12 for maneuvering extension cannula 10.

Self-expanding conduit 12 has inlet 16 at its proximal end and outlet 14 at its distal end, and a lumen extending therethrough for permitting blood flow. Self-expanding conduit 12 has a length sufficient to extend from the outlet the conventional VA-ECMO cannula to a position above the patient's renal arteries, and more preferably, into the thoracic aorta, e.g., 15-120 cm or preferably 20-80 cm. As described more fully below, self-expanding conduit 12 includes a self-expanding support structure, such as a mesh, weave or braid, covered by a flexible and biocompatible covering. Moreover, as shown in FIG. 1A, self-expanding conduit 12 may include one or more radiopaque markers 18 disposed along the distal end of self-expanding conduit 12 adjacent outlet 14 to permit its location to be determined fluoroscopically. In addition, the biocompatible covering in the vicinity of the distal end of self-expanding conduit 12 may be omitted to permit blood to exit laterally therethrough and perfuse the thoracic aorta.

Figure 1B:
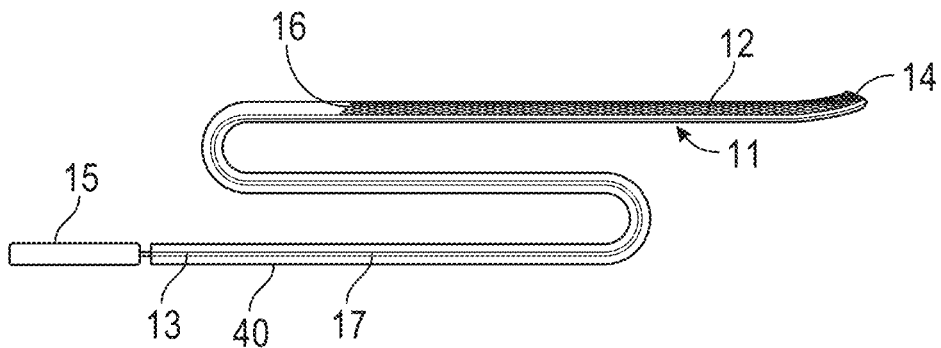
FIG. 1B is a side view of the extension cannula of FIG. 1A, with the extension conduit in a contracted state within the delivery sheath.

The support structure of self-expanding conduit 12 may be made of a wire mesh, weave or braid formed of a shape-memory metal or stainless steel, such that self-expanding conduit 12 may transition from a collapsed insertion state and an expanded deployed state. As depicted in FIG. 1B, the support structure of the conduit may be formed of a stainless steel mesh, weave or braid having a preset expanded diameter that forms a central lumen, such that the conduit may be contracted when pulled within smaller diameter delivery sheath 40. Alternatively, the support structure may be a mesh, weave or braid formed of a shape-memory metal such as a nickel-titanium alloy ("Nitinol"), and having a predetermined expanded diameter that forms the internal lumen. In this way, the conduit may be contracted to the collapsed insertion state when pulled within delivery sheath 40 as described in further detail below.

The support structure preferably is encapsulated with a biocompatible polymer coating, such as expanded polytetrafluoroethylene ("ePTFE"). In the expanded deployed state, self-expanding conduit 12 assumes a diameter substantially the same as, or even larger than, the internal lumen of a conventional VA-ECMO cannula, and thus does not require a larger-bore opening in the femoral vasculature. For example, the lumen of self-expanding conduit 12 may range from 15 Fr to 25 Fr in the expanded state. When inserted through a conventional ECMO cannula, self-expanding conduit 12 permits enhanced blood flow to the ascending aorta and aortic arch, while maintaining the diameter of the vascular opening in the femoral artery required to introduce the conventional VA-ECMO return cannula. In some embodiments, the biocompatible polymer coating may include pores that permit blood to perfuse laterally through the material, thereby reducing jetting from outlet 14.

Still referring to FIG. 1A, in one preferred embodiment, inlet 16 at the proximal end of self-expanding conduit 12 may have a feature for facilitating recapture of self-expanding conduit 12 within the delivery sheath. For example, as shown in FIG. 1A, self-expanding conduit 12 may have tapered geometry 19 that facilitates retrieval of self-expanding conduit 12. For example, the support structure of self-expanding conduit 12 may include a laterally displaced wire hoop that resides along the edge of inlet 16, thereby forming tapered geometry 19. Alternatively, the distal end of shaft 17 may be coupled to support legs coupled to the proximal end of the support structure of self-expanding conduit 12, such that advancing a sheath over the support legs causes the support structure of self-expanding conduit 12 to collapse inwardly to the collapsed insertion state as described in further detail below. In addition, the distal end of self-expanding conduit 12 may include an atraumatic region.

Figure 2:
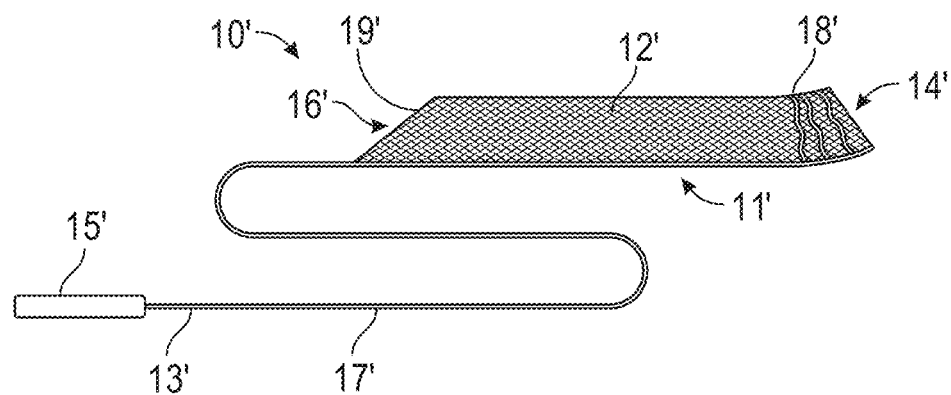
FIG. 2 is a side view of an alternative embodiment of the extension cannula of FIG. 1A, with the extension conduit in an expanded state and the delivery sheath removed.

Referring now to FIG. 2, alternative embodiment of extension cannula 10' of the present invention is described. In this embodiment, conduit 12' is made of a soft flexible material, such as polyethylene, polyurethane, or nylon, and may include pores that permit some blood to perfuse laterally through the material while directing the bulk of the flow through conduit 12' to outlet 14'. Elongated shaft 17' serves as a spine to assist in passing extension conduit 12' through the lumen of a conventional ECMO cannula, and to position inlet 16' near the outlet of the ECMO cannula, and outlet 14' in distal region 11' above a patient's renal arteries, and more preferably, extending into the patient's thoracic aorta. Shaft 17' may be coupled to handle 15' for maneuvering device 10'. Conduit 12' preferably includes at its proximal end a self-expanding support hoop 19' that expands the opening 16' at proximal end of conduit 12' when released from a delivery sheath, as described above with respect to FIG. 1B. Conduit 12' may include radiopaque markers 18' near outlet 14'. Support hoop 19' ensures that blood flowing through the conventional ECMO cannula is funneled into the proximal end of conduit 12' and causes the remainder of conduit 12' to fully open. As for the embodiment of FIG. 1A, conduit 12' may be collapsed at the conclusion of a reperfusion procedure by advancing sheath 40 distally over elongated shaft 17' and conduit 12'.

Figure 3A:
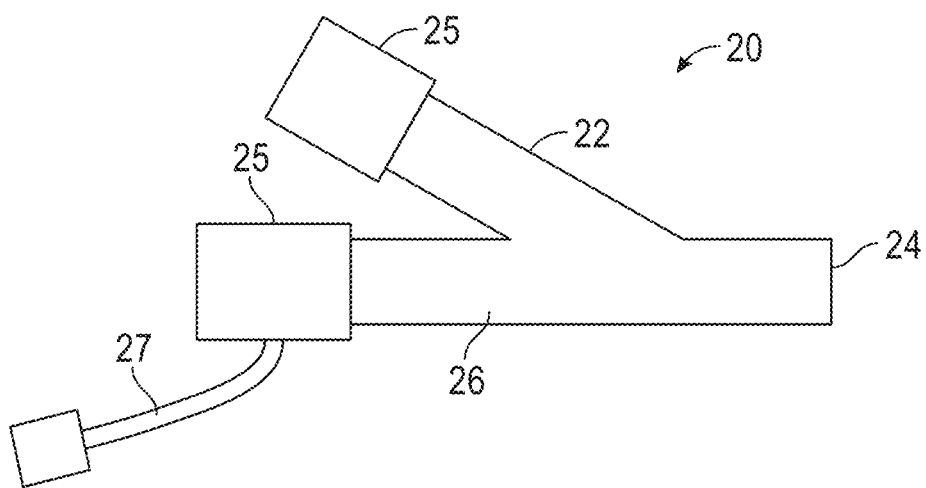
FIG. 3A is a schematic view of an exemplary in-line connector configured for use with the extension cannulas of the present invention.

With respect to FIG. 3A, in-line connector 20 suitable for use with the extension cannula of the present invention is described. In-line connector 20 has first branch inlet 22 configured to be coupled to an outlet of a conventional ECMO machine for receiving oxygenated blood from an ECMO circuit, second branch inlet 26 having a hemostatic valve welded therein, and outlet 24 configured to be coupled to a conventional ECMO cannula. First branch inlet 22 and second branch inlet 26 each are in fluid communication with outlet 24, and each may include an optional hemostatic valve 25, as described below with respect to FIG. 3B. The fluid pathway extending between first branch inlet 22 and outlet 24 thus permits oxygenated blood received from an ECMO circuit to flow to through the conventional ECMO cannula and self-expanding conduit 12. Moreover, the fluid pathway extending between second branch inlet 26 and outlet 24 is sized and shaped to permit delivery therethrough of self-expanding conduit 12 in a collapsed insertion state, e.g., when disposed within delivery sheath 40. Accordingly, extension cannula 10 or 10' of FIGS. 1 and 2 may be inserted through the hemostatic valve of second branch inlet 26 and advanced through the lumen of the conventional ECMO return cannula coupled to outlet 24.

As will be understood by a person of ordinary skill in the art, the fluid pathway extending between second branch 26 and outlet 24 may be sized and shaped to permit delivery of other interventional tools therethrough as well, including, e.g., a catheter for coronary, peripheral, or cerebral vascular or valvular interventions, and/or a pneumatic, rotary, or transvalvular flow pump. Delivery of extension cannula 10 or 10' and other large-bore interventional devices or small catheters is possible due to co-linearity of second branch inlet 26 with outlet 24. Unlike previously known Y-shaped connectors used in interventional procedures, the linear alignment of second branch inlet 26 and outlet 24 of in-line connector 20 permits a device to be inserted without bending. Accordingly, the linear alignment of second branch inlet 26 and outlet 24 of in-line connector 20 accommodates delivery of large bore devices, e.g., a delivery catheter for a transcatheter aortic valve replacement (TAVR) valve, an Impella pump, or smaller catheters such as coronary, cerebral, or peripheral vascular interventional guide catheters.

In-line connector 20 may be removably coupled to the conventional ECMO return cannula when the extension cannula or other interventional devices are required to be delivered, e.g., by clamping the ECMO return cannula, decoupling the ECMO return cannula from the ECMO circuit, coupling in-line connector 20 to the ECMO circuit and the ECMO return cannula via first branch inlet 22 and outlet 24, respectively, and unclamping the ECMO return cannula. Advantageously, in-line connector 20 enables extension of existing short ECMO cannulas, adjustment of location of the extension cannula within the aorta, and removal of the extension cannula without disrupting ECMO flow. Alternatively, in-line connector 20 may be integrally constructed as part of the ECMO return cannula, e.g., a 15, 17, 19, 21, or 25 Fr conventional ECMO return cannula. Accordingly, in-line connector 20 may include an end cap coupled second branch inlet 26 when no device is delivered therethrough. As described above, second branch inlet 26 may include a hemostatic valve to prevent backflow of blood during delivery of the extension cannula or other interventional device, and the end cap may be coupled to second branch inlet 26 to prevent further exposure of the hemostatic valve. Advantageously, the single built cannula enables rapid delivery of flow above the renal vessels without the need for an in-line connector and also enables positioning of the extension cannula along the length of the aorta.

Also shown in FIG. 3A is optional side arm 27 coupled to, and in fluid communication with, second branch inlet 26. Side arm 27 may be used for flushing of in-line connector 20 or may be used to fluidly couple in-line connector 20 to an antegrade perfusion catheter to perfuse the patient's lower extremities to protect against limb ischemia. For example, an antegrade perfusion catheter may be inserted via side arm 27, through in-line connector 20 and the convention ECMO return cannula, and positioned within the patient such that oxygenated blood is delivered to the patient's lower extremities.

Figure 3B:
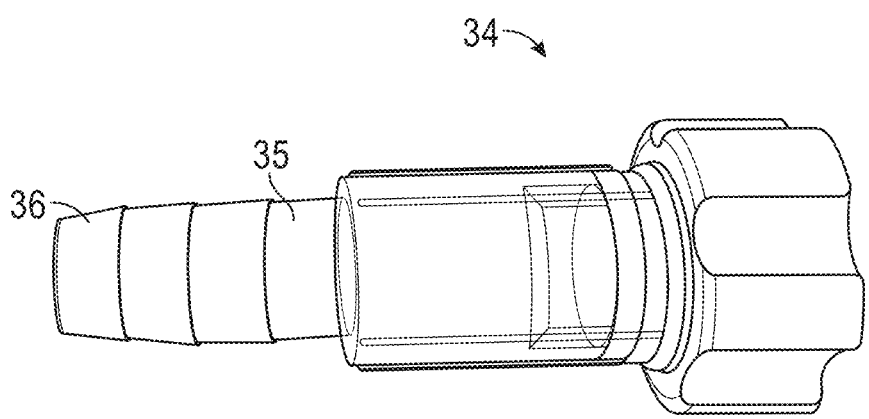
FIG. 3B illustrates an end cap for use with the in-line connector of FIG. 3A.

In accordance with another aspect of the invention, a variety of end caps and tubing adapters may be provided for use with second branch inlet 26 of in-line connector 20. For example, hemostatic valve 25 may have a diameter, e.g., a ⅜ inch, sized for selectively closing off second branch inlet 26 when not in use. Alternatively, an end cap may include a double hemostatic valve, as depicted in FIG. 3B, for preventing backflow of blood through second branch inlet 26 of in-line connector 20 when extension catheter is inserted therethrough. As a further alternative, an end cap may have stopper portion having a length that extends substantially for the length of the lumen of second branch inlet 26, such that it prevents blood from pooling in the lumen of second branch inlet 26.

Referring now to FIG. 3B, end cap 34 includes adapter portion 35 that may be inserted into the outlet tubing of a conventional ECMO system. End cap 34 preferably includes internal lumen 36 having a diameter smaller than the lumen of second branch inlet 26, and suitable for, e.g., drug infusion or pressure/flow monitoring. Moreover, end cap 34 may include a hemostatic valve positioned within lumen 36 to prevent backflow of blood therethrough. As will be understood by a person of ordinary skill in the art, alternatively or in addition to a hemostatic valve, end cap 34 may include, e.g., a screw (aperture) valve, a balloon valve, a double membrane valve, etc. Alternatively, lumen 36 may have a diameter selected depending on which procedure is desired. End cap 34 may be coupled to a second arm of in-line connector 20 described above to permit delivery of interventional tools and/or removal of an existing ECMO cannula therethrough as described above. End cap 34 may be, e.g., a screw cap, that may be rotatably coupled to the in-line connector and/or existing ECMO cannula.

In accordance with another aspect of the present invention, end cap 34 may be incorporated directly into an existing ECMO cannula. For example, instead of use of an in-line connector to couple the existing ECMO cannula with the ECMO circuit, end cap 34 may be coupled to the existing ECMO cannula directly, e.g., either as two separate components coupled together or an integral component, such that the existing ECMO cannula is in fluid communication with the ECMO circuit via end cap 34. As described above, end cap 34 may include one or more hemostatic valves to prevent backflow of blood therethrough. If an existing ECMO cannula needs to be removed and/or replaced, e.g., to exchange an existing ECMO cannula for a larger diameter ECMO cannula, the existing ECMO cannula may be removed through the lumen of end cap 34.

For example, at the time an ECMO cannula needs to be removed, a clamp may be applied to the ECMO circuit so that the ECMO circuit may be decoupled from end cap 34. A guidewire then may be introduced through the lumen of end cap 34. The existing ECMO cannula may be removed over the guidewire, and a new, larger ECMO cannula, e.g., a 19 Fr cannula, may be advanced over the guidewire through the lumen of end cap 34, and positioned within the patient's vasculature. The ECMO circuit may then be recoupled to end cap 34 and unclamped to permit blood to once again flow from the ECMO circuit through the new, larger ECMO cannula. Similarly, the ECMO circuit may be decoupled from end cap 34 in the manner described above when interventional tool(s) need to be delivered to the patient, and recoupled when the interventional procedure is complete.

Figure 4A:
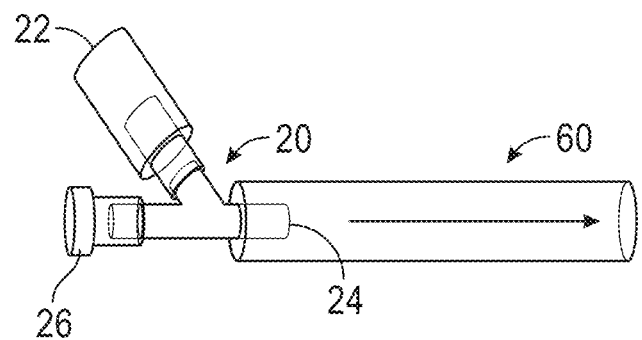
FIGS. 4A-4C are schematic views illustrating use of an exemplary in-line connector with the extension cannula FIG. 1A in an ECMO system.
Figure 4B:
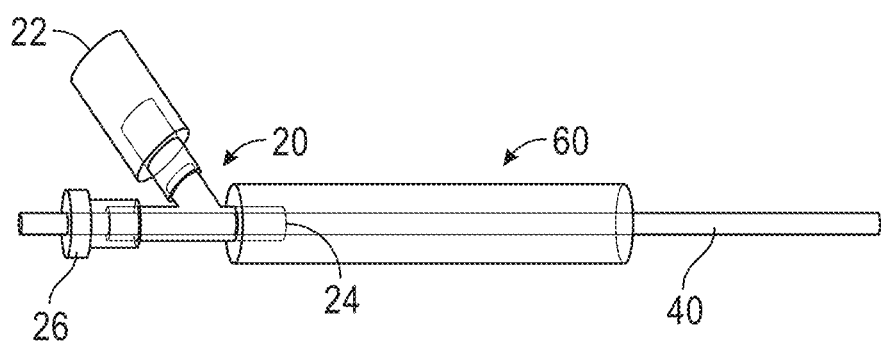
Figure 4C:
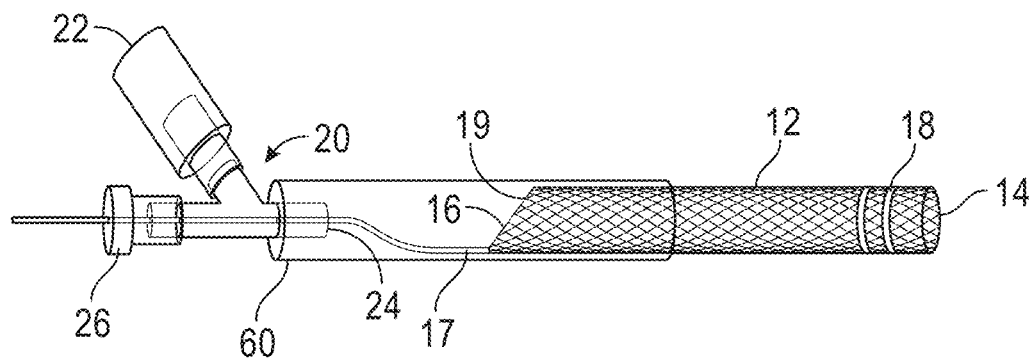

Referring now to FIGS. 4A to 4C, operation of the embodiment of the extension cannula of FIGS. 1A and 1B is schematically depicted in conjunction with in-line connector 20 of FIG. 3A. First, conventional ECMO cannula 60 is coupled to outlet 24 of in-line connector 20 and inserted into a patient's arterial vasculature, e.g., via a cut down to the femoral artery, as shown in FIG. 4A. The outlet line from an ECMO machine is coupled to first branch inlet 22. As shown in FIG. 4B, extension cannula 10, disposed with self-expanding conduit 12 in its collapsed insertion state within delivery sheath 40, is advanced through the hemostatic valve of second branch inlet 26 of in-line connector 20. Extension cannula 10 is positioned so that the distal end of self-expanding conduit 12 is disposed in the desired location, e.g., within the thoracic aorta, and the proximal end of self-expanding conduit 12 lies near the distal outlet of the conventional ECMO return catheter, e.g., as may be determined under fluoroscopy using, e.g., radiopaque marker bands disposed on sheath 40.

The lumen of sheath 40 preferably is dimensioned to accept and retain self-expanding conduit 12 in its collapsed insertion state. For example, the lumen of sheath 40 may have a diameter between 1.40 mm and 1.50 mm, and more preferably 1.45 mm. Sheath 40 has an outer diameter sized to it to be readily inserted through the lumen of a conventional VA-ECMO return cannula. Sheath 40 is slidably disposed over self-expanding conduit 12 so that it may be retracted relative to self-expanding conduit 12, thereby permitting self-expanding conduit 12 to self-expand from the collapsed insertion state to the expanded, deployed state.

Referring now to FIG. 4C, when sheath 40 and self-expanding conduit 12 are positioned in the desired location as described above, sheath 40 is retracted while self-expanding conduit 12 is held in position by elongated shaft 17 and handle 15, thereby permitting self-expanding conduit 12 to transition to its expanded, deployed state. Because most of the length of self-expanding conduit 12 extends past the distal end of conventional ECMO return cannula 60, oxygenated blood from the ECMO machine may be delivered to regions beyond those accessible with a conventional ECMO return cannula. In accordance with one aspect of the present invention, other interventional tools, e.g., vascular catheters, valve catheters, or intra-aortic or trans-valvular pumps, e.g., Impella® pump (made available by Abiomed, Danvers, Mass.), also may be inserted through the ECMO cannula via second branch inlet 26 of in-line connector 20 to perform additional interventional procedures simultaneously with VA-ECMO. Moreover, arterial repair tools may delivered to the patient's vasculature through the in-line connector to facilitate removal of, e.g., an arterial cannula. For example, the in-line connector may be used to provide wire re-access to the native femoral vessel, thereby allowing for removal of the ECMO cannula and delivery of vascular closure devices at the time of ECMO decannulation, thereby avoiding the need for surgical repair of the vessel.

In one preferred embodiment of extension cannula 10, self-expanding conduit 12 has a length between 20 to 80 cm or longer. In this manner, blood may be delivered in the vicinity of a patient's thoracic aorta, above the patient's renal artery ostia, to avoid high flow rates in the vicinity of the patient's renal arteries and reduce the risk of perfusion injury. In addition, if the distal end of self-expanding conduit 12 is disposed in the ascending aorta, as may be determined under fluoroscopy using radiopaque marker bands 18, outflow from self-expanding conduit 12 can provide oxygenated blood to the cardiac arteries in the vicinity of the aortic root and also provide antegrade flow to the carotid arteries and downstream arteries.

Still referring to FIG. 4C, when the patient is to be removed from ECMO, sheath 40 may be re-inserted over elongated shaft 17 and advanced to collapse and retrieve self-expanding conduit 12. In this case, sheath 40 will first engage tapered proximal end 19 of self-expanding conduit 12, such that advancement of sheath 40 while retaining shaft 17 stationary will cause self-expanding conduit 12 to collapse inward and return to its reduced diameter, collapsed insertion state. Extension cannula 10 and sheath 40 may then be removed through the hemostatic valve within second branch inlet 26. Use and operation of the embodiment of FIG. 2 is substantially the same as described above.

Figure 4D:
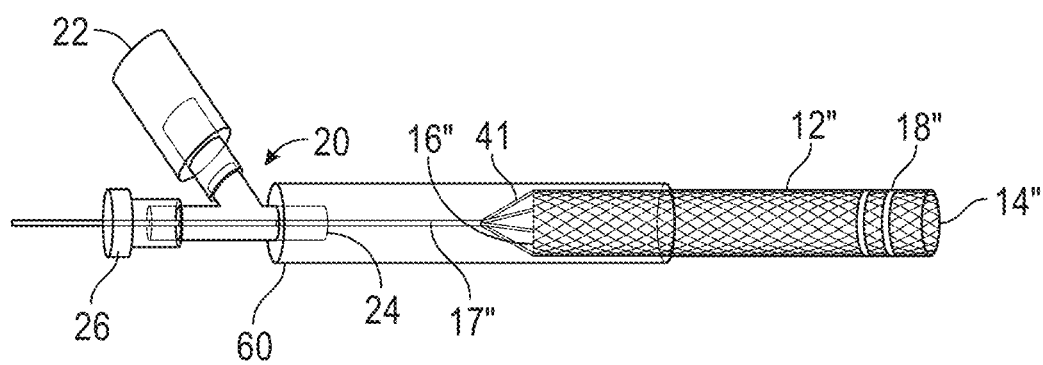
FIG. 4D is a schematic view illustrating use of an exemplary in-line connector with an alternative exemplary extension cannula in an ECMO system.

Referring now to FIG. 4D, a further alternative embodiment of an extension cannula and sheath constructed in accordance with the principles of the present invention is described. Self-expanding conduit 12" is constructed similar to self-expanding conduit 12 of FIG. 4C. For example, self-expanding conduit 12" has inlet 16", outlet 14", and one or more radiopaque marker bands 18", which correspond with inlet 16, outlet 14, and bands 18 of self-expanding conduit 12, respectively. Self-expanding conduit 12" differs from self-expanding conduit 12 in that, instead of tapered inlet geometry 19, self-expanding conduit 12" has plurality of angled legs 41 that couple self-expanding conduit 12" to elongated shaft 17" to facilitate resheathing for removal. Preferably, angled legs 41 are flexible and of uniform length, so that when the distal end of sheath 40 is advanced over angled legs 41, the legs flex inward to cause the support structure of self-expanding conduit 12" to collapse inward.

Moreover, sheath 40 may have a rapid exchange configuration, with sheath 40 having a length suitable for covering the entire length of self-expanding conduit 12, 12" but is joined to a support shaft and a handle coupled to the end of the support shaft. In this manner, sheath 40 may be back-loaded over the proximal end of elongated shaft 17, 17" of the extension cannula and manipulated using the support shaft via the handle, without interfering with the ability to manipulate the proximal end of shaft 17, 17".

Still referring to FIG. 4D, operation for the alternative embodiment of the extension cannula is similar to that of the embodiment of FIGS. 4A to 4C. As shown in FIG. 4D, self-expanding conduit 12" and sheath 40 are advanced through in-line connector 20 (see FIG. 4B) and into the lumen of conventional ECMO return cannula 60 with self-expanding conduit 12" in the collapsed insertion state within sheath 40. Sheath 40 is withdrawn proximally while self-expanding conduit 12" is retained stationary using elongated shaft 17", thereby permitting self-expanding conduit 12" to self-expand to its predetermined diameter, as shown in FIG. 4D. Once sheath 40 is fully withdrawn, blood flow through conventional ECMO return catheter 60 is directed through angled legs 41 to the outlet of self-expanding conduit 12", which flex outward as the support structure of self-expanding conduit 12" self-expands. When the ECMO procedure is completed, blood flow from the ECMO machine is paused. Sheath 40 then is back-loaded over elongated shaft 17" of the extension cannula, and advanced distally using the support shaft of sheath 40 as described above. When the distal end of sheath 40 contacts angled legs 41, it causes the legs to flex inwardly and the proximal end of the support structure of self-expanding conduit 12" to transition to its insertion diameter. Accordingly, further distal advancement of sheath 40 causes the remaining length of self-expanding conduit 12" to transition to the collapsed insertion state, thereby facilitating removal of the extension cannula.

Figure 5:
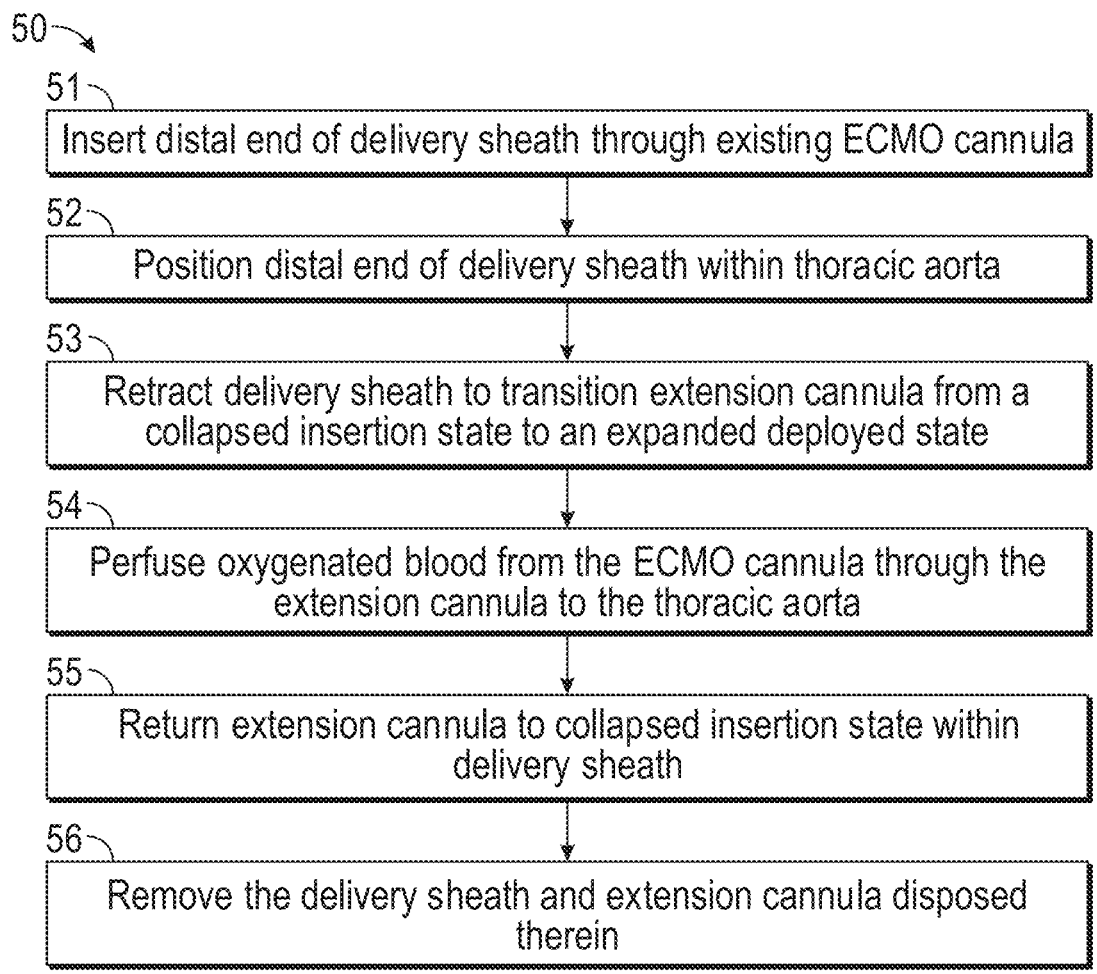
FIG. 5 is a flow chart of exemplary steps for improving perfusion during ECMO in accordance with the principles of the present invention.
Figure 6A:
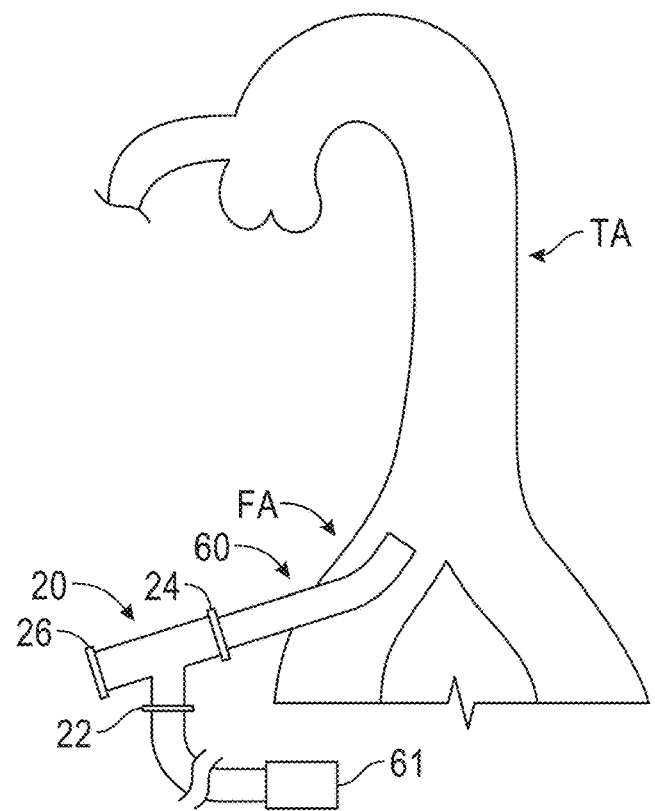
FIGS. 6A-6E illustrate the exemplary steps for improving perfusion during ECMO using the extension cannula of FIG. 1A.
Figure 6B:
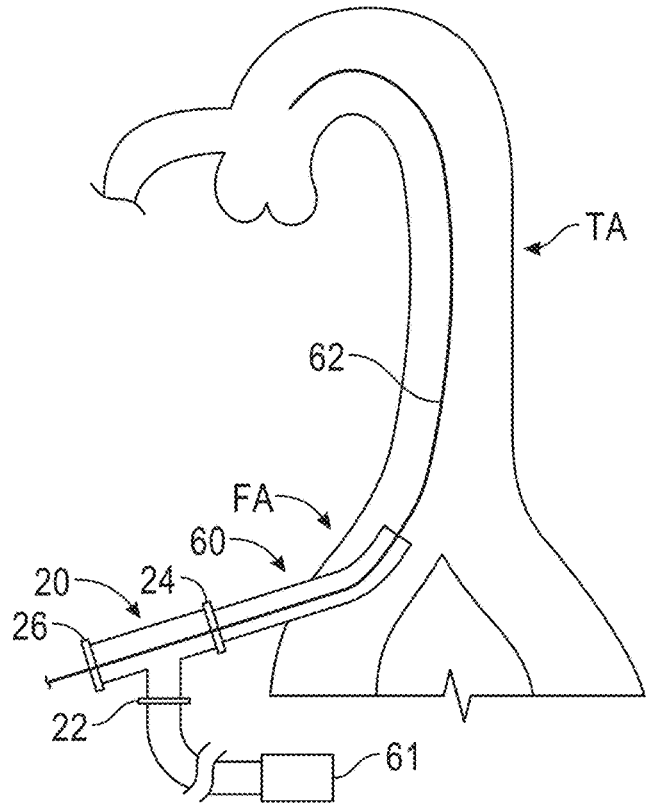

Referring now to FIG. 5, a flow chart of exemplary steps for improving perfusion during ECMO in accordance with the principles of the present invention is provided. Some of the steps of method 50 may be further elaborated by referring to FIGS. 6A to 6E. For example, FIG. 6A illustrates conventional ECMO cannula 60 inserted through the patient's femoral artery FA coupled to ECMO machine 61 via outlet 24 and first inlet 22 of in-line connector 20 as described above. As shown in FIG. 6B, guidewire 62 may be inserted through second branch inlet 26 and outlet 24 of in-line connector 20, and through ECMO cannula 60 until the distal end of guidewire 62 is advanced to the desired location within the patient's vasculature, e.g., within the thoracic aorta TA such as within the ascending aorta or in the vicinity of the aortic arch.

Figure 6C:
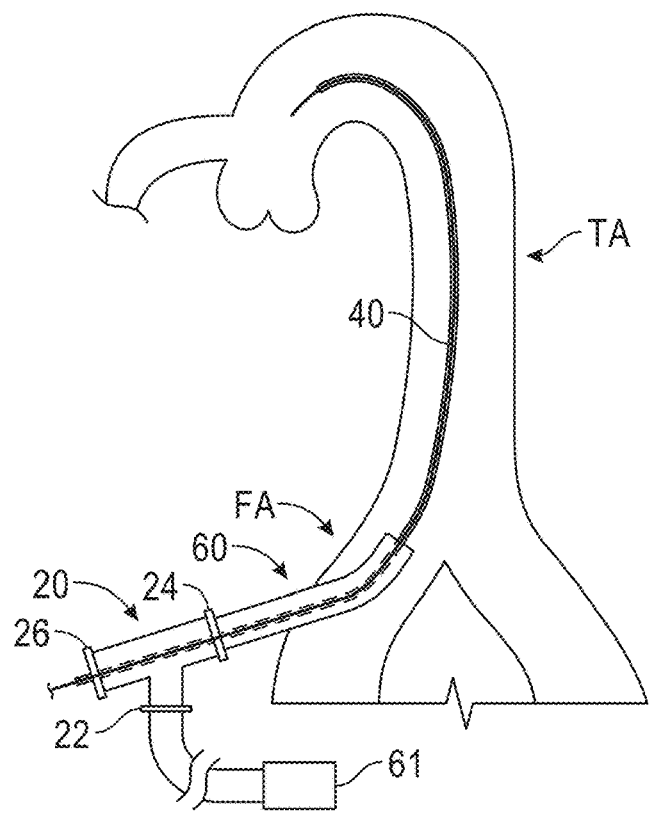
Figure 6D:
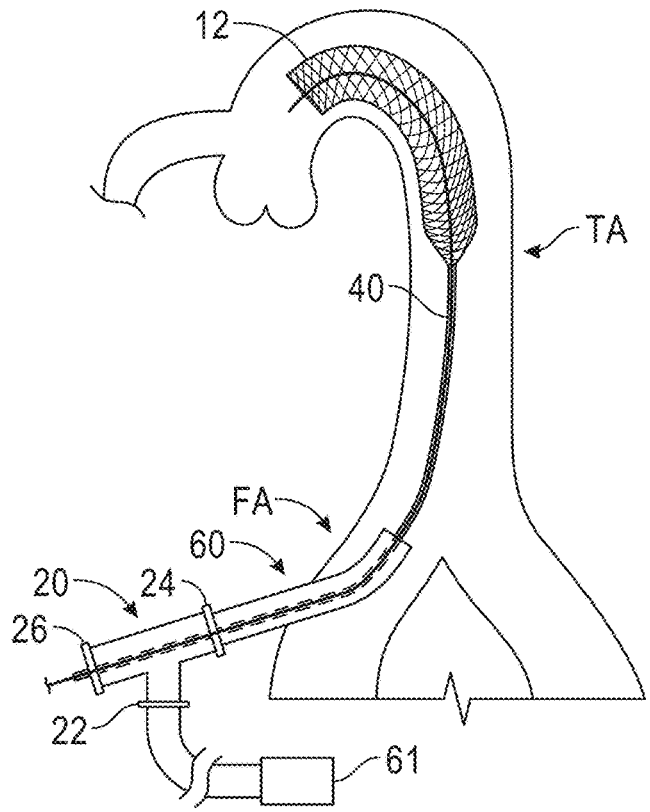
Figure 6E:
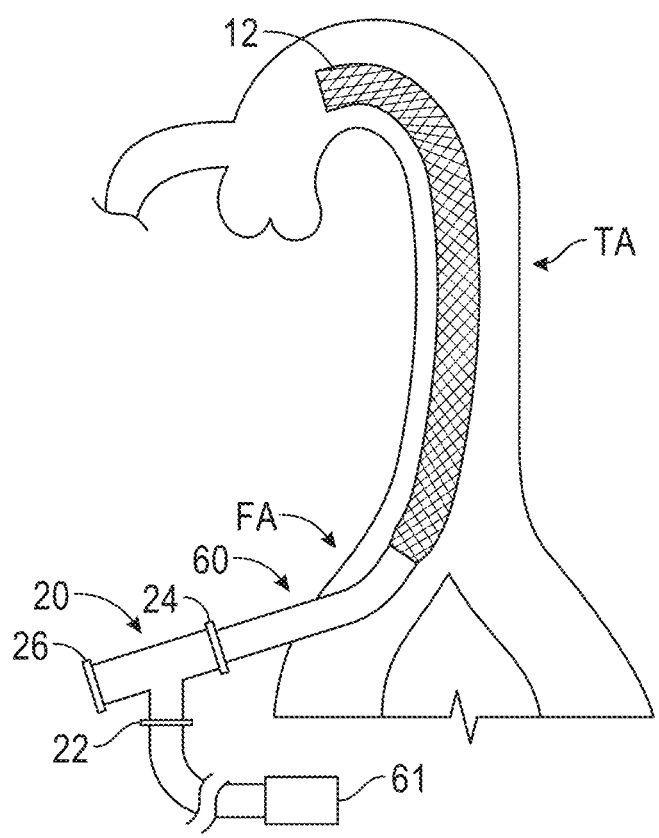

At step 51, the distal end of sheath 40, having self-expanding conduit 12 disposed therein in a collapsed insertion state, is advanced through ECMO cannula 60, e.g., over guidewire 62, via in-line connector 20. The distal end of sheath 40 is advanced until it is positioned at the desired central location within the patient's vasculature at step 52 as shown in FIG. 6C. At step 53, sheath 40 is retracted relative to self-expanding conduit 12 slidably disposed within the lumen of sheath 40, while self-expanding conduit 12 remains stationary, causing self-expanding conduit 12 to transition from the collapsed insertion state to an expanded deployed state as shown in FIGS. 6D and 6E. FIG. 6D illustrates self-expanding conduit 12 partially fully expanded within the patient's vasculature, and FIG. 6E illustrates self-expanding conduit 12 fully expanded within the patient's vasculature, e.g., when self-expanding conduit 12 is fully exposed from sheath 40. Accordingly, at step 54, oxygenated blood may be perfused from ECMO cannula 60 to the central location within the patient's vasculature, e.g., within the ascending aorta or in the vicinity of the aortic arch. As a result, blood flow into the adjacent vessels, e.g., the coronary arteries and/or the carotid arteries, will occur and with a more normal antegrade flow pattern. As will be understood by a person of ordinary skill in the art, the outlet of self-expanding conduit 12 may be positioned within the descending aorta, e.g., the portion of the descending aorta approaching the level of the diaphragm from beneath the thoracic cavity or the portion of the descending aorta above the diaphragm.

In accordance with one aspect of the present invention, the ECMO pump may be programmed to generate a pulsatile flow to create pressure fluctuations at the outlet of self-expanding conduit 12 that mimics the patient's heartbeat. As a result, the patient may receive significant benefits such as retaining the elasticity of the arteries and reducing arterial stiffening, as opposed to with continuous flow. When the ECMO therapy is complete, at step 55, self-expanding conduit 12 may be returned to the collapsed insertion state within the lumen of sheath 40 as described above, and at step 56, sheath 40 and self-expanding conduit 12 disposed therein may be removed from the patient.

Figure 7A:
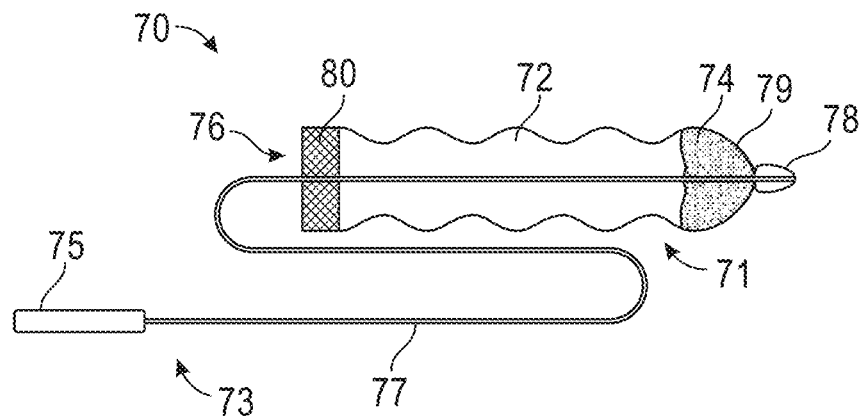
FIG. 7A is a side view of an alternative exemplary extension cannula for improving reperfusion during ECMO, constructed in accordance with the principles of the present invention, with the extension conduit in a partially collapsed state.
Figure 7B:
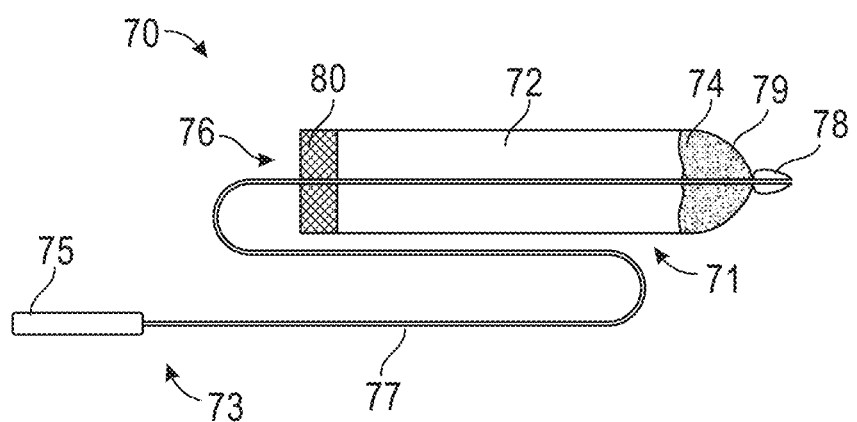
FIG. 7B is a side view of extension cannula of FIG. 7A in an expanded state.

Referring now to FIGS. 7A and 7B, an alternative exemplary extension cannula suitable for use with a conventional VA-ECMO cannula is described. Extension cannula 70 includes elongated shaft 77, e.g., a hypotube, extending between distal region 71 and proximal region 73 of extension cannula 70. Hypotube 77 is formed of a material, e.g., stainless steel rod, having sufficient rigidity to permit extension cannula 70 to be advanced through a conventional ECMO reperfusion cannula so that distal region 71 of expandable conduit 72 may be disposed with its outlet extending beyond a patient's renal arteries, and preferably extending in a patient's ascending aorta or in the vicinity of the aortic arch. For example, hypotube 77 may have a lumen sized and shaped to receive a guidewire therethrough, such that extension cannula 70 may be advanced through the conventional ECMO reperfusion cannula to the target location over a guidewire via the lumen of hypotube 77. Extension cannula 70 optionally may include handle 75 coupled to hypotube 77 at proximal region 73 of extension cannula 70 for maneuvering extension cannula 70.

The distal end of hypotube 77 may include atraumatic tip 78, which may be coupled to the distal region of expandable conduit 72 via connection structure 79, e.g., one or more umbrella-like struts. Connection structure 79 may be self-expandable between a collapsed delivery state and an expanded deployed state, e.g., upon exposure from sheath 40. As shown in FIGS. 7A and 7B, connection structure 79 may have a curved shape in the expanded deployed state. Connection structure 79 may be embedded within the biocompatible material forming expanding conduit 72. Additionally or alternatively, connection structure 79 may be coupled to the inner surface of expandable conduit 72 or to the outer surface of expandable conduit 72, or both. Hypotube 77 does not form part of the blood flow path through the lumen of expandable conduit 72. In one embodiment, connection structure 79 is not self-expandable, such that connection structure 79 transitions from the collapsed delivery state to the expanded deployed state when blood flows through the lumen of expandable conduit 72, thereby causing expandable conduit 72 to fill with blood.

Expandable conduit 72 is made of a soft flexible material, such as polyethylene, polyurethane, or nylon, and may include pores 74 at its distal region that permit blood to perfuse through the material as the flow is directed through the lumen of expandable conduit 72. For example, expandable conduit 72 has inlet 76 at its proximal end and an outlet, e.g., plurality of pores 74, at its distal region, and a lumen extending therethrough for permitting blood flow. Pores 74 may be sized and shaped such that, as blood flows from the ECMO machine and through the conventional ECMO reperfusion cannula and the lumen of expandable conduit 72, the blood flow exits expandable conduit 72 via pores 74, while causing expandable conduit 72 to fill with blood and transition from a collapsed delivery state, as shown in FIG. 7A, to the expanded deployed state, as shown in FIG. 7B. Moreover, expandable conduit 72 has a length sufficient to extend from the outlet of the conventional ECMO reperfusion cannula to a position above the patient's renal arteries, and more preferably, into the thoracic aorta, e.g., 15-120 cm, or preferably 20-80 cm or 30-50 cm. Notably, the lightweight sock-like structure provides advantages including, for example, ease of deployment through tortuous or diseased aortas, as well as no impingement on the spinal cord as most patients are lying flat such that use of a rigid cannula may impinge on the spinal cord.

In addition, expandable conduit 72 may include a self-expanding support structure, e.g., anchoring stent 80, such as a mesh, weave or braid formed of a shape-memory metal or stainless steel, at its proximal end such that anchoring stent 80 may transition from a collapsed insertion state and an expanded deployed state within the lumen of the conventional ECMO reperfusion cannula to thereby anchor expandable conduit 72 within the conventional ECMO reperfusion cannula. For example, anchoring stent 80 may be biased toward the expandable deployed state, such that anchoring stent 80 may self-expand upon exposure from sheath 40. Anchoring stent 80 may be covered by a flexible and biocompatible covering, or alternatively, anchoring stent 80 may be uncovered. Anchoring stent 80 may be formed of a stainless steel mesh, weave or braid having a preset expanded diameter that forms a central lumen, such that expandable conduit 72 may be contracted when pulled within smaller diameter delivery sheath 40. Alternatively, anchoring stent 80 may be a mesh, weave or braid formed of a shape-memory metal such as a nickel-titanium alloy ("Nitinol"), and having a predetermined expanded diameter that forms the internal lumen. In this way, expandable conduit 72 may be contracted to the collapsed insertion state when pulled within delivery sheath 40 as described in further detail below.

In the fully expanded deployed state, anchoring stent 80 assumes a diameter substantially the same as, or even larger than, the internal lumen of a conventional VA-ECMO cannula. For example, the lumen of anchoring stent 80 may be at least 15 Fr in the expanded state. Accordingly, when deployed within the lumen of the conventional ECMO cannula, anchoring stent 80 will expand to the diameter of the lumen of the conventional ECMO cannula, such that anchoring stent 80 will apply a radially outward force against the inner surface of the conventional ECMO cannula to thereby anchor anchoring stent 80 within the lumen of the conventional ECMO cannula. When inserted through a conventional ECMO cannula and anchored to the conventional ECMO cannula via anchoring stent 80, expandable conduit 72 permits enhanced blood flow to the ascending aorta and aortic arch, while maintaining the diameter of the vascular opening in the femoral artery required to introduce the conventional VA-ECMO return cannula. In some embodiments, the biocompatible polymer coating may include additional pores proximal to pores 74 that permit blood to perfuse laterally through the material, thereby reducing jetting from pores 74. Like self-expanding conduit 12, expandable conduit 72 may include one or more radiopaque markers disposed along the distal end of expandable conduit 72 adjacent pores 74 to permit its location to be determined fluoroscopically.

In some embodiments, like self-expanding conduit 12" of FIG. 4D, inlet 76 at the proximal end of expandable conduit 72 may have a feature for facilitating recapture of expandable conduit 72 within the delivery sheath. For example, expandable conduit 72 may have a plurality of angled legs that couple anchoring stent 80 of expandable conduit 72 to shaft 77 to facilitate resheathing of expandable conduit 72 for removal. Preferably, the angled legs are flexible and of uniform length, so that when the distal end of sheath 40 is advanced over the angled legs, the legs flex inward to cause anchoring stent 80 to collapse inward toward its collapsed delivery state. Alternatively, when expandable conduit 72 does not have a feature for facilitating recapture of expandable conduit 72, expandable conduit 72 may be removed along with the conventional ECMO cannula by turning off the ECMO machine to stop blood flow into expandable conduit 72, thereby causing expandable conduit 72 to return to a semi-collapsed state. Accordingly, expandable conduit 72 and the conventional ECMO cannula may be removed together from the patient's vasculature.

As described above, sheath 40 may have a rapid exchange configuration, with sheath 40 having a length suitable for covering the entire length of expandable conduit 72 but is joined to a support shaft and a handle coupled to the end of the support shaft. In this manner, sheath 40 may be backloaded over the proximal end of shaft 77 of extension cannula 70 and manipulated using the support shaft via the handle, without interfering with the ability to manipulate the proximal end of shaft 77.

Figure 8A:
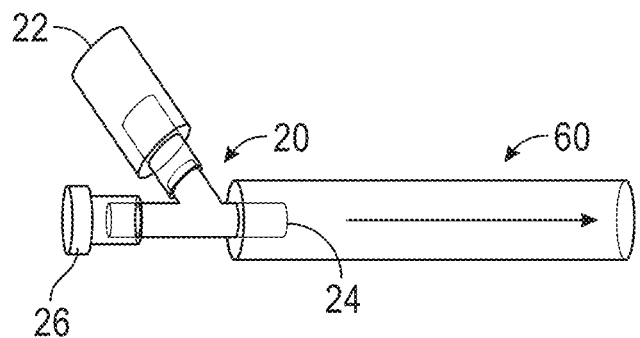
FIGS. 8A-8C are schematic views illustrating use of an exemplary in-line connector with the extension cannula of FIGS. 7A and 7B in an ECMO system.
Figure 8B:
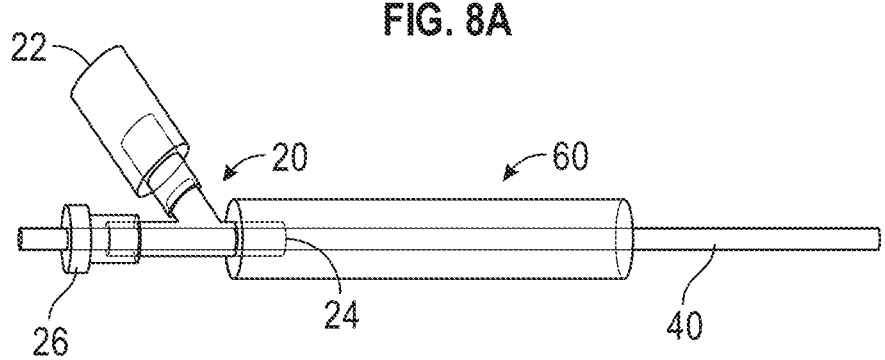
Figure 8C:
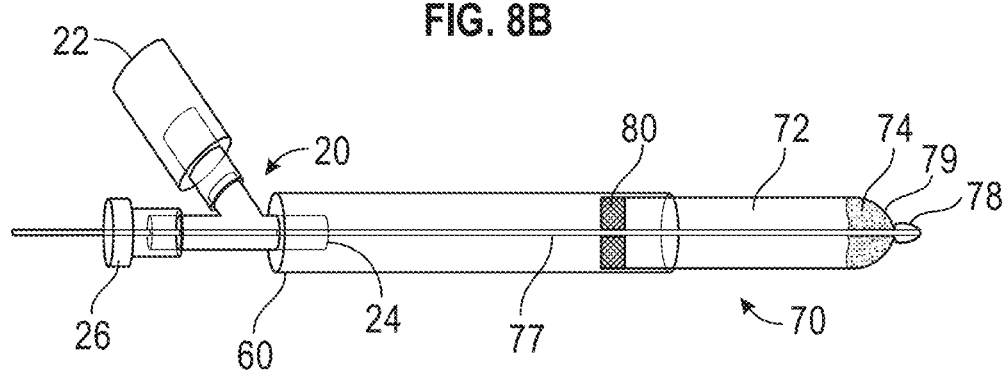

Referring now to FIGS. 8A to 8C, operation of the embodiment of the extension cannula of FIGS. 7A and 7B is schematically depicted in conjunction with an optional in-line connector 20 of FIG. 3A. As described above with regard to FIGS. 4A and 4B, conventional ECMO cannula 60 may be coupled to outlet 24 of in-line connector 20 and inserted into a patient's arterial vasculature, e.g., via a cut down to the femoral artery, as shown in FIG. 8A. The outlet line from an ECMO machine may be coupled to first branch inlet 22. As shown in FIG. 8B, extension cannula 70, disposed with expandable conduit 72 in its collapsed insertion state within delivery sheath 40, is advanced through the hemostatic valve of second branch inlet 26 of in-line connector 20. Extension cannula 70 is positioned so that the distal end of expandable conduit 72 is disposed in the desired location, e.g., within the thoracic aorta, and the proximal end of expandable conduit 72 lies near the distal outlet of the conventional ECMO reperfusion cannula, e.g., as may be determined under fluoroscopy using, e.g., radiopaque marker bands disposed on sheath 40.

The lumen of sheath 40 preferably is dimensioned to accept and retain expandable conduit 72 in its collapsed insertion state. Sheath 40 is slidably disposed over expandable conduit 72, and accordingly anchoring stent 80 and connection structure 79, so that sheath 40 may be retracted relative to expandable conduit 72, thereby permitting connection structure 79 and/or anchoring stent 80 to transition from the collapsed delivery state to the expanded deployed state upon exposure from sheath 40.

Referring now to FIG. 8C, when sheath 40 and expandable conduit 72 are positioned in the desired location as described above, sheath 40 is retracted while expandable conduit 72 is held in position by hypotube 77 and handle 75, thereby permitting connection structure 79 and/or anchoring stent 80 to transition to their expanded, deployed states. As shown in FIG. 8C, in its expanded deployed state, anchoring stent 80 abuts the inner surface of conventional ECMO reperfusion cannula 60 to thereby anchor expandable conduit 72 within conventional ECMO reperfusion cannula 60. Initially, upon retraction of sheath 40 and expansion of connection structure 79 and/or anchoring stent 80, the portion of expandable conduit 72 between connection structure 79 and anchoring stent 80 may still be in a semi-collapsed delivery state, as shown in FIG. 7A. Expandable conduit 72 may fully transition to its expanded deployed state when in fluid communication with blood flow from the ECMO machine through conventional ECMO reperfusion cannula 60, as shown in FIG. 7B. For example, in a fully expanded state, expandable conduit 72 may have a diameter of 10-20 mm.

Referring again to FIG. 8C, because most of the length of expandable conduit 72 extends past the distal end of conventional ECMO reperfusion cannula 60, oxygenated blood from the ECMO machine may be delivered, e.g., via pores 74, to regions beyond those accessible with a conventional ECMO return cannula. In one preferred embodiment of extension cannula 70, expandable conduit 72 has a length between 15 to 120 cm or preferably, 20-80 cm or longer. In this manner, blood may be delivered in the vicinity of a patient's thoracic aorta, above the patient's renal artery ostia, to avoid high flow rates in the vicinity of the patient's renal arteries and reduce the risk of perfusion injury. In addition, if the distal end of expandable conduit 72 is disposed in the ascending aorta, as may be determined under fluoroscopy using radiopaque marker bands disposed on expandable conduit 72, outflow from pores 74 of expandable conduit 72 can provide oxygenated blood to the cardiac arteries in the vicinity of the aortic root and also provide antegrade flow to the carotid arteries and downstream arteries. Accordingly, ECMO reperfusion cannula 60 may be shortened compared with conventional ECMO cannulas, e.g., 5-15 cm, or preferably 8-10 cm.

As described above, when the patient is to be removed from ECMO, sheath 40 may be re-inserted over shaft 77 and advanced to collapse and retrieve expandable conduit 72. In this case, sheath 40 will first engage the plurality of angled legs that couple anchoring stent 80 of expandable conduit 72 to shaft 77, such that advancement of sheath 40 while retaining shaft 77 stationary will cause anchoring stent 80, and accordingly expandable conduit 72, to collapse inward and return to its reduced diameter, collapsed insertion state within sheath 40. As sheath 40 is further advanced distally over expandable conduit 72, sheath 40 will engage with and cause connection structure 79 to collapse inward and return to its collapsed insertion state, such that expandable conduit 72 is disposed within sheath 40. Extension cannula 70 and sheath 40 may then be removed through the hemostatic valve within second branch inlet 26.

Figure 8D:
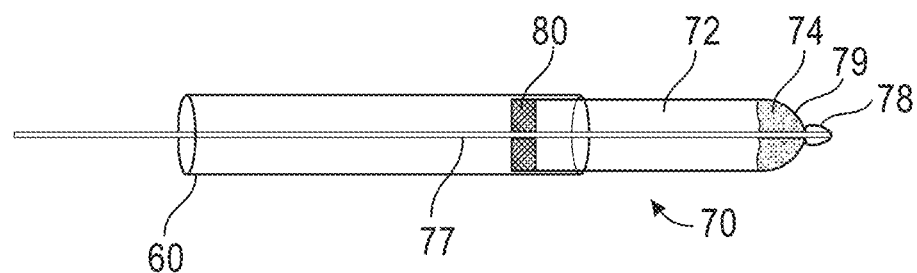
FIG. 8D is a schematic view illustrating use of the extension cannula of FIGS. 7A and 7B in an ECMO system.

FIG. 8D illustrates extension cannula 70 coupled to conventional ECMO reperfusion cannula 60 without in-line connector 20. As described above, in-line connector 20 is optional. Accordingly, the proximal end of conventional ECMO reperfusion cannula 60 may be coupled directly to the ECMO circuit.

Figure 9A:
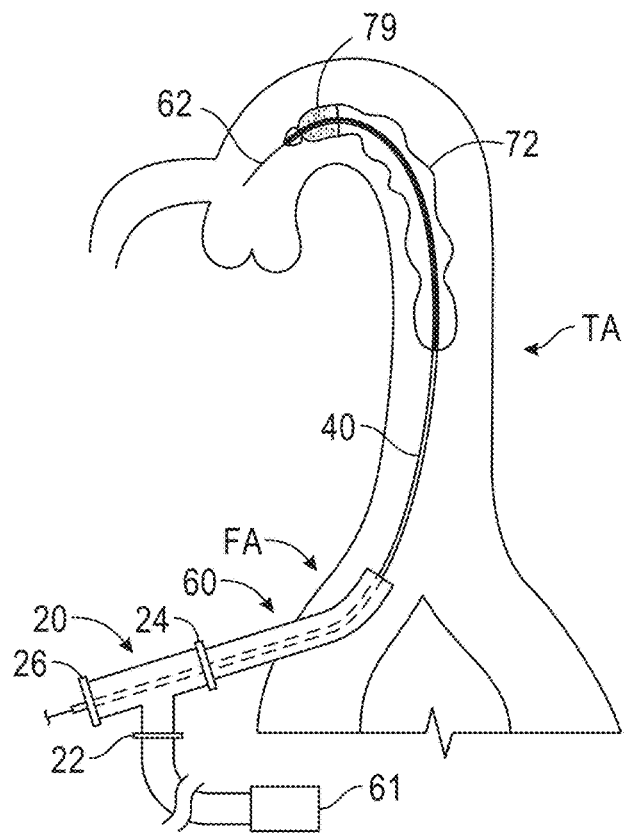
FIGS. 9A and 9B illustrate exemplary steps for improving perfusion during ECMO using the extension cannula of FIGS. 7A and 7B and an exemplary in-line connector.
Figure 9B:
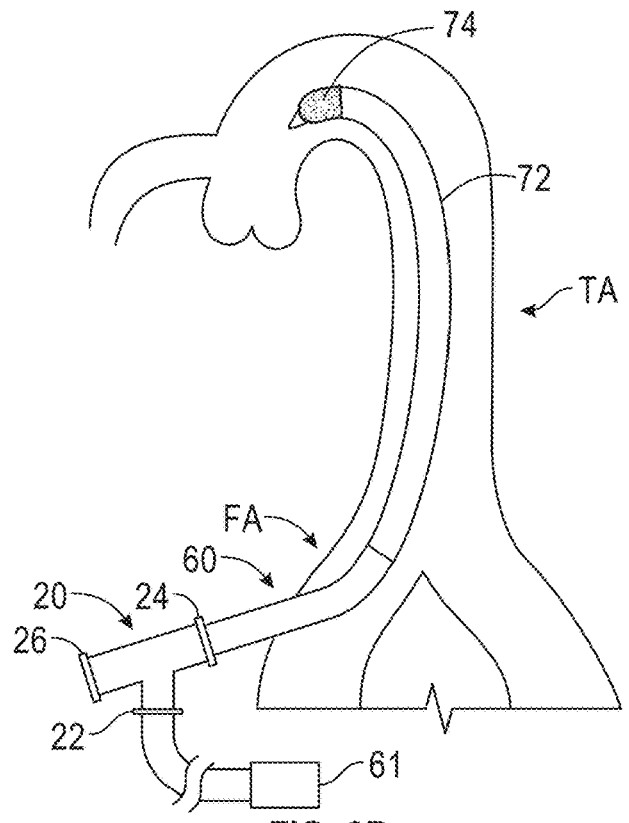

Referring now to FIGS. 9A and 9B, exemplary steps for improving perfusion during ECMO using the extension cannula of FIGS. 7A and 7B are provided. Specifically, method steps 51-56 of FIG. 5 described above may be used to deliver extension cannula 70 for improving perfusion during ECMO. Initially, the distal region of extension cannula 70 may be delivered to the target location within the thoracic aorta in a collapsed insertion state within sheath 40, as described above with regard to steps 51 and 52 of FIG. 5, and as illustrated by FIGS. 6A to 6C. For example, conventional ECMO cannula 60 may be inserted through the patient's femoral artery FA coupled to ECMO machine 61 via outlet 24 and first inlet 22 of in-line connector 20, and guidewire 62 may be inserted through second branch inlet 26 and outlet 24 of in-line connector 20, and through ECMO cannula 60 until the distal end of guidewire 62 is advanced to the desired location within the patient's vasculature, e.g., within the thoracic aorta TA such as within the ascending aorta or in the vicinity of the aortic arch. At step 51, the distal end of sheath 40, having expandable conduit 72 disposed therein in a collapsed insertion state, is advanced through ECMO cannula 60, e.g., over guidewire 62, via the lumen of hypotube 77 and in-line connector 20. The distal end of sheath 40 is advanced until it is positioned at the desired central location within the patient's vasculature at step 52 as shown in FIG. 6C.

At step 53, sheath 40 is retracted relative to expandable conduit 72 slidably disposed within the lumen of sheath 40, while expandable conduit 72 remains stationary, causing connection structure 79, and accordingly at least a portion of expandable conduit 72, to transition from the collapsed insertion state to an expanded deployed state upon exposure from sheath 40, as shown in FIG. 9A. FIG. 9A illustrates expandable conduit 72 in a semi-expanded state within the patient's vasculature. Sheath 40 is further retracted relative to expandable conduit 72, causing anchoring stent 80 to transition from the collapsed insertion state to an expanded deployed state upon exposure from sheath 40 within ECMO cannula 60, thereby anchoring expandable conduit 72 to ECMO cannula 60. FIG. 9B illustrates expandable conduit 72 fully expanded within the patient's vasculature, e.g., when expandable conduit 72 is fully exposed from sheath 40 and blood flows from the ECMO machine through ECMO cannula 60 and into the lumen of expandable conduit 72.

When expandable conduit 72 is fully deployed within the patient's vasculature, at step 54, oxygenated blood may be perfused from ECMO cannula 60 to the central location within the patient's vasculature, e.g., within the ascending aorta or in the vicinity of the aortic arch, via pores 74 at the distal region of expandable conduit 72. As will be understood by a person of ordinary skill in the art, pores 74 of expandable conduit 72 may be positioned within the descending aorta, e.g., the portion of the descending aorta approaching the level of the diaphragm from beneath the thoracic cavity or the portion of the descending aorta above the diaphragm. When the ECMO therapy is complete, at step 55, expandable conduit 72 may be returned to the collapsed insertion state within the lumen of sheath 40 as described above, and at step 56, sheath 40 and expandable conduit 72 disposed therein may be removed from the patient.

Figure 10A:
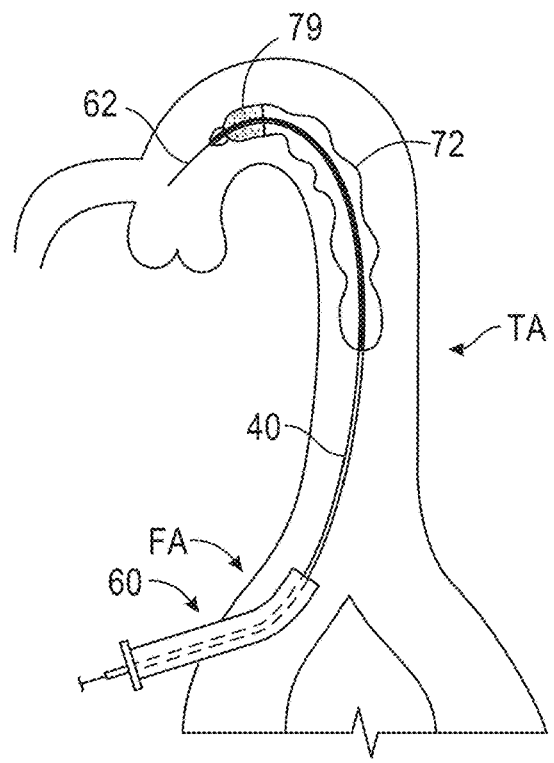
FIGS. 10A and 10B illustrate exemplary steps for improving perfusion during ECMO using the extension cannula of FIGS. 7A and 7B.
Figure 10B:
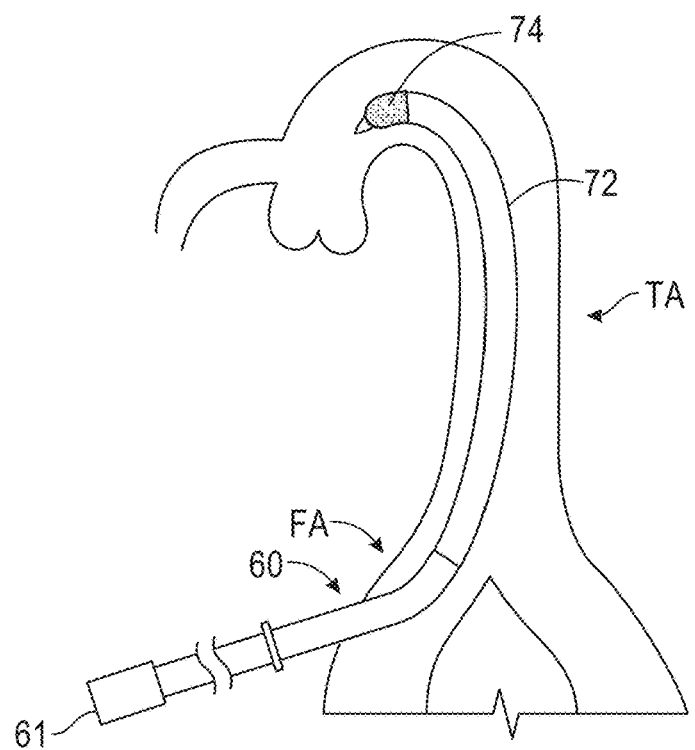

Referring now to FIGS. 10A and 10B, exemplary steps for improving perfusion during ECMO using the extension cannula of FIG. 8D are provided. Specifically, method steps 51-56 of FIG. 5 described above may be used to deliver extension cannula 70 for improving perfusion during ECMO. Initially, the distal region of extension cannula 70 may be delivered to the target location within the thoracic aorta in a collapsed insertion state within sheath 40, as described above with regard to steps 51 and 52 of FIG. 5. For example, conventional ECMO cannula 60 may be inserted through the patient's femoral artery FA. Preferably, conventional ECMO cannula 60 is not yet coupled to ECMO machine 61 at this stage. Next, guidewire 62 may be inserted through ECMO cannula 60 until the distal end of guidewire 62 is advanced to the desired location within the patient's vasculature, e.g., within the thoracic aorta TA such as within the ascending aorta or in the vicinity of the aortic arch. At step 51, the distal end of sheath 40, having expandable conduit 72 disposed therein in a collapsed insertion state, is advanced through ECMO cannula 60, e.g., over guidewire 62, via the lumen of hypotube 77. The distal end of sheath 40 is advanced until it is positioned at the desired central location within the patient's vasculature at step 52 as shown in FIG. 6C. Guidewire 62 may then be removed through the proximal end of hypotube 77.

At step 53, sheath 40 is retracted relative to expandable conduit 72 slidably disposed within the lumen of sheath 40, while expandable conduit 72 remains stationary, causing connection structure 79, and accordingly at least a portion of expandable conduit 72, to transition from the collapsed insertion state to an expanded deployed state upon exposure from sheath 40, as shown in FIG. 10A. FIG. 10A illustrates expandable conduit 72 in a semi-expanded state within the patient's vasculature. Sheath 40 is further retracted relative to expandable conduit 72, causing anchoring stent 80 to transition from the collapsed insertion state to an expanded deployed state upon exposure from sheath 40 within ECMO cannula 60, thereby anchoring expandable conduit 72 to ECMO cannula 60. The proximal end of ECMO cannula 60 may then be coupled to ECMO machine 61, e.g., via tubing.

FIG. 10B illustrates expandable conduit 72 fully expanded within the patient's vasculature, e.g., when expandable conduit 72 is fully exposed from sheath 40 and blood flows from ECMO machine 61 through ECMO cannula 60 and into the lumen of expandable conduit 72. As described above, when expandable conduit 72 is fully deployed within the patient's vasculature, at step 54, oxygenated blood may be perfused from ECMO cannula 60 to the central location within the patient's vasculature, e.g., within the ascending aorta or in the vicinity of the aortic arch, via pores 74 at the distal region of expandable conduit 72. When the ECMO therapy is complete, at step 55, expandable conduit 72 may be returned to the collapsed insertion state within the lumen of sheath 40 as described above, and at step 56, sheath 40 and expandable conduit 72 disposed therein may be removed from the patient.

Figure 11A:
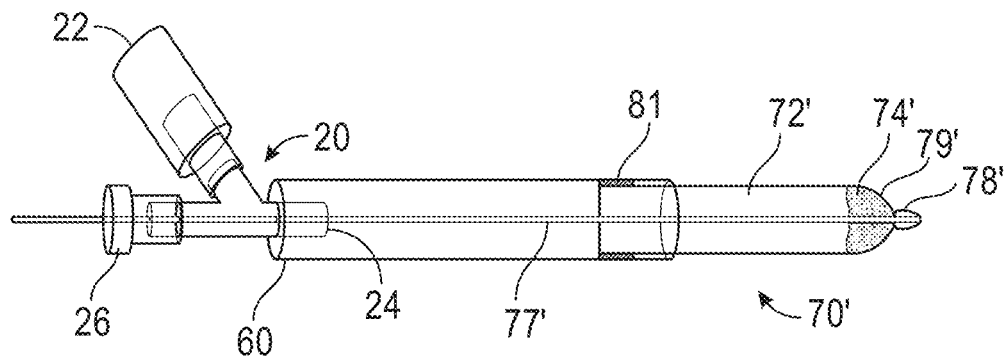
FIG. 11A is a schematic view illustrating use of an exemplary in-line connector with an alternative exemplary extension cannula in an ECMO system, constructed in accordance with the principles of the present invention, where a proximal end of the extension cannula is coupled to a conventional ECMO cannula.

Referring now to FIG. 11A, another alternative exemplary extension cannula is provided. Extension cannula 70' may be constructed similar to the extension cannula 70, except that the proximal end of expandable conduit 72' may be fixed to conventional ECMO reperfusion cannula 60 prior to insertion of extension cannula 70' into the patient. For example, as shown in FIG. 11A, the proximal end of expandable conduit 72' may be coupled to the inner surface of conventional ECMO reperfusion cannula 60 via coupling mechanism 81, e.g., an adhesive. Accordingly, extension cannula 70', conventional ECMO reperfusion cannula 60, and in-line connector 20, are advanced together into the patient, e.g., by guiding tip 78' of extension cannula 70' via hypotube 77', to position pores 74' of expandable conduit 72' in the vicinity of the aortic root, as described in further detail below.

Figure 11B:
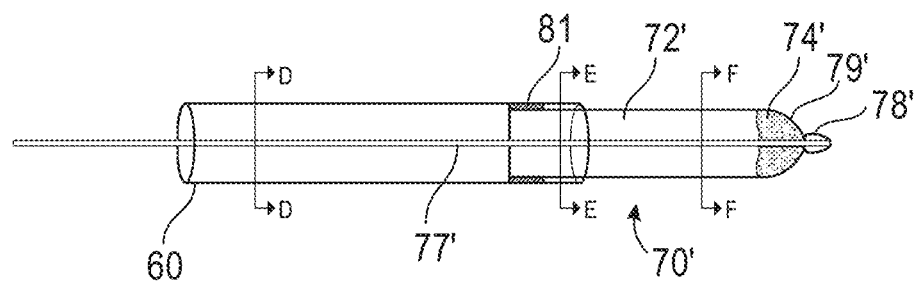
FIG. 11B is a schematic view illustrating use of the extension cannula of FIG. 11A in an ECMO system without an in-line connector.

FIG. 11B illustrates extension cannula 70' coupled to conventional ECMO reperfusion cannula 60 without in-line connector 20. As described above, in-line connector 20 is optional. Accordingly, the proximal end of conventional ECMO reperfusion cannula 60 may be coupled directly to the ECMO circuit. As shown in FIGS. 11D to 11F, hypotube 77' may be positioned on a single side within the lumens of expandable conduit 72' and ECMO cannula 60. Specifically, FIG. 11D illustrates a cross-sectional view of extension cannula 70' along line D-D of FIG. 11B, FIG. 11E illustrates a cross-sectional view of extension cannula 70' along line E-E of FIG. 11B, and FIG. 11F illustrates a cross-sectional view of extension cannula 70' along line F-F of FIG. 11B. As shown in FIG. 11D, hypotube 77' may be positioned against an inner wall of ECMO cannula 60 within the proximal region of ECMO cannula 60. As shown in FIG. 11E, hypotube 77' may be positioned against an inner wall of expandable conduit 72' within the distal region of ECMO cannula 60, e.g., adjacent to where expandable conduit 72' is coupled to ECMO cannula 60 via coupling mechanism 81. As shown in FIG. 11D, hypotube 77' may be positioned against an inner wall of expandable conduit 72' throughout the length of expandable conduit 72'. Accordingly, hypotube 77' may extend from tip 78', and along an inner surface of hypotube 77' toward ECMO cannula 60.

Figure 11C:
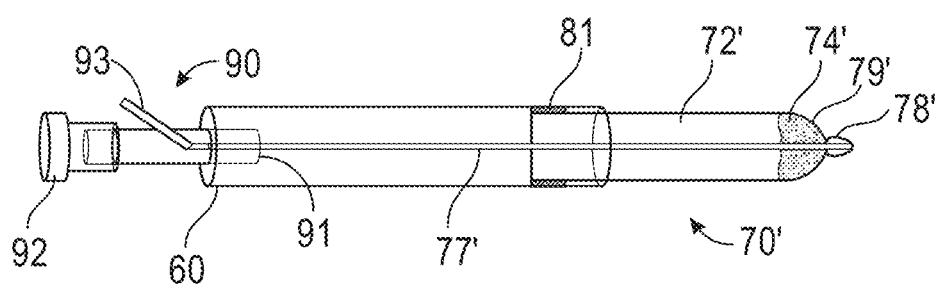
FIG. 11C is a schematic view illustrating use of an exemplary connector having a side arm with the extension cannula of FIG. 11A in an ECMO system.
Figure 11F:
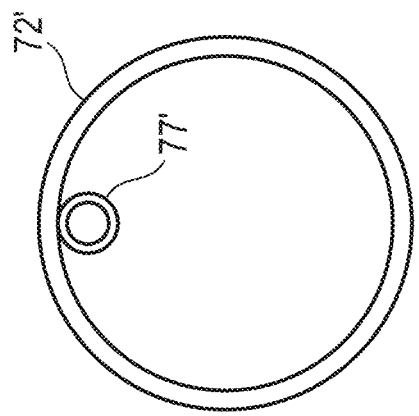
FIGS. 11D to 11F are cross-sectional views of the extension cannula of FIG. 11B.
Figure 11E:
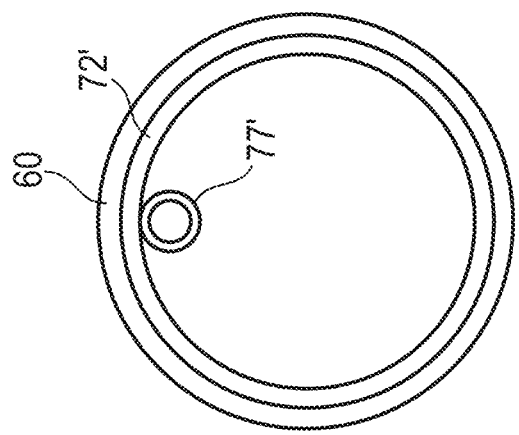
Figure 11D:
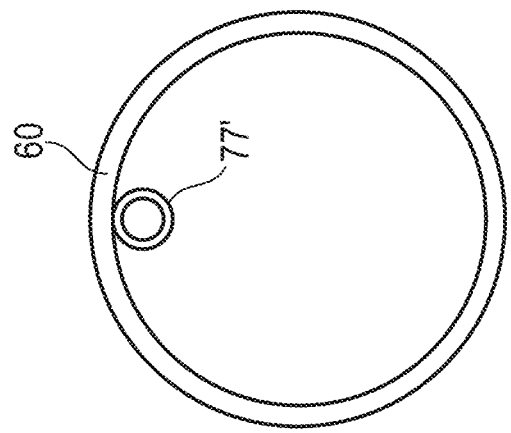

Referring now to FIG. 11C, another exemplary connector for use with the extension cannulas described herein is provided. Connector 90 may have inlet 92 configured to be coupled to an outlet of a conventional ECMO machine for receiving oxygenated blood from an ECMO circuit, sidearm 93 extending at an angle from a side of connector 90, and outlet 91 configured to be coupled to a conventional ECMO cannula. Inlet 92 is in fluid communication with outlet 91, and may include an optional hemostatic valve 25, as described above with respect to FIG. 3B. The fluid pathway extending between inlet 92 and outlet 91 thus permits oxygenated blood received from an ECMO circuit to flow to through the conventional ECMO cannula and expandable conduit 72'. As shown in FIG. 11C, inlet 92 may be co-linear with outlet 91. Moreover, sidearm 93 is in fluid communication with the lumen of hypotube 77', and also may have an optional hemostatic valve welded therein. Accordingly, sidearm 93 may have a lumen sized and shaped to receive a guidewire therethrough. In addition, sidearm 93 and hypotube 77' may be sized and shaped to receive a stylet therein, the stylet configured to be inserted through sidearm 93 and hypotube 77' to preserve the lumen of sidearm 93 and hypotube 77' during operation and prevent clotting therein. Additionally, upon removal of the stylet, the guidewire may be reinserted through sidearm 93 and hypotube 77' for removal of extension cannula 70'.

Figure 12:
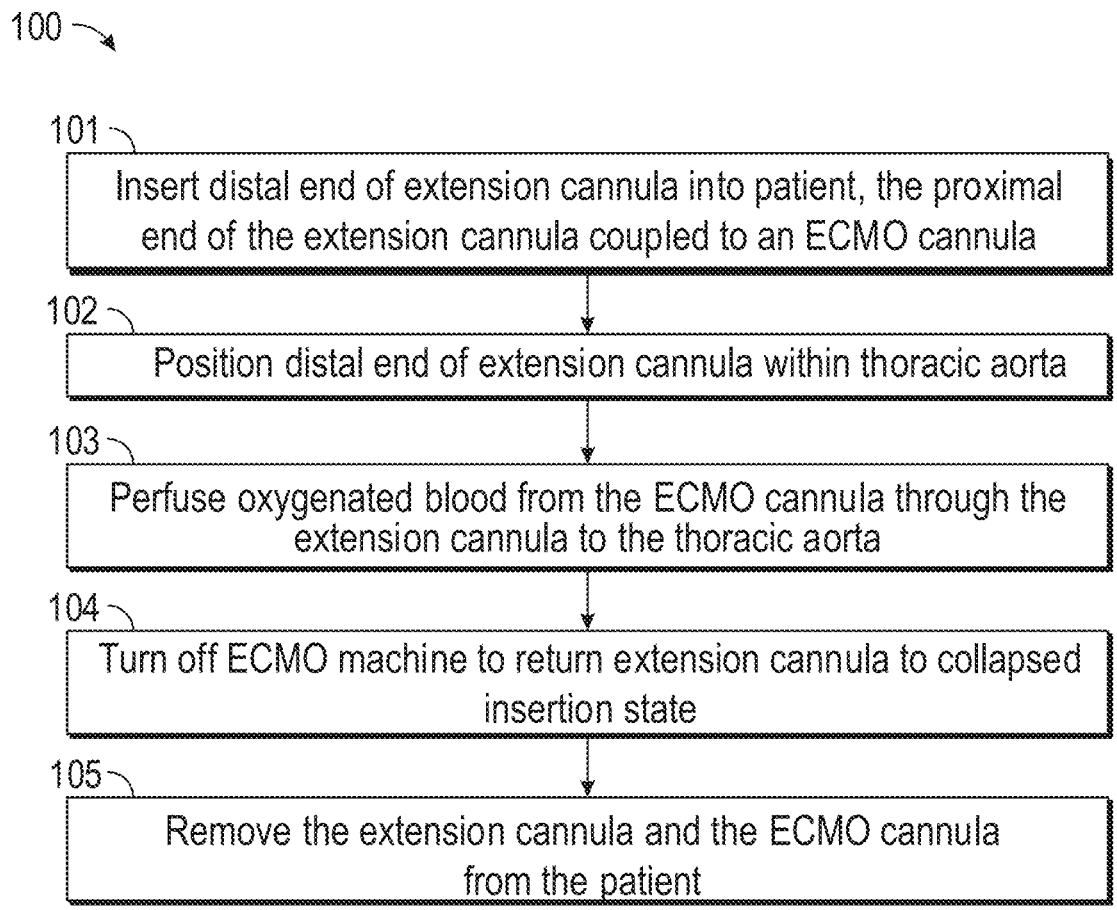
FIG. 12 is a flow chart of exemplary steps for improving perfusion during ECMO using the extension cannula of FIGS. 11A to 11C in accordance with the principles of the present invention.

Referring now to FIG. 12, a flow chart of exemplary steps for improving perfusion during ECMO using any one of the extension cannulas of FIGS. 11A to 11C is provided. Some of the steps of method 100 may be further elaborated by referring to FIGS. 13A and 13B, as well as FIGS. 14A to 15B, as described in further detail below. As described above, expandable conduit 72' is coupled to ECMO cannula 60 prior to insertion of extension cannula 70' and ECMO cannula 60 into the patient. Accordingly, referring to the extension cannula of FIG. 11A, hypotube 77' may extend from tip 78' proximally through the lumen of expandable conduit 72', the lumen of ECMO cannula 60, outlet 24 of in-line connector 20, and second branch inlet 26 of in-line connector 20. Moreover, ECMO cannula 60 is coupled to ECMO machine 61 via outlet 24 and first inlet 22 of in-line connector 20. Initially, guidewire 62 may be inserted through hypotube 77' such that guidewire 62 passes through second branch inlet 26 and outlet 24 of in-line connector 20, through ECMO cannula 60, and through the lumen and tip 78' of expandable conduit 72'. Guidewire 62 may be advanced through an incision in the patient's femoral artery FA until the distal end of guidewire 62 is advanced to the desired location within the patient's vasculature, e.g., within the thoracic aorta TA such as within the ascending aorta or in the vicinity of the aortic arch.

Figure 13A:
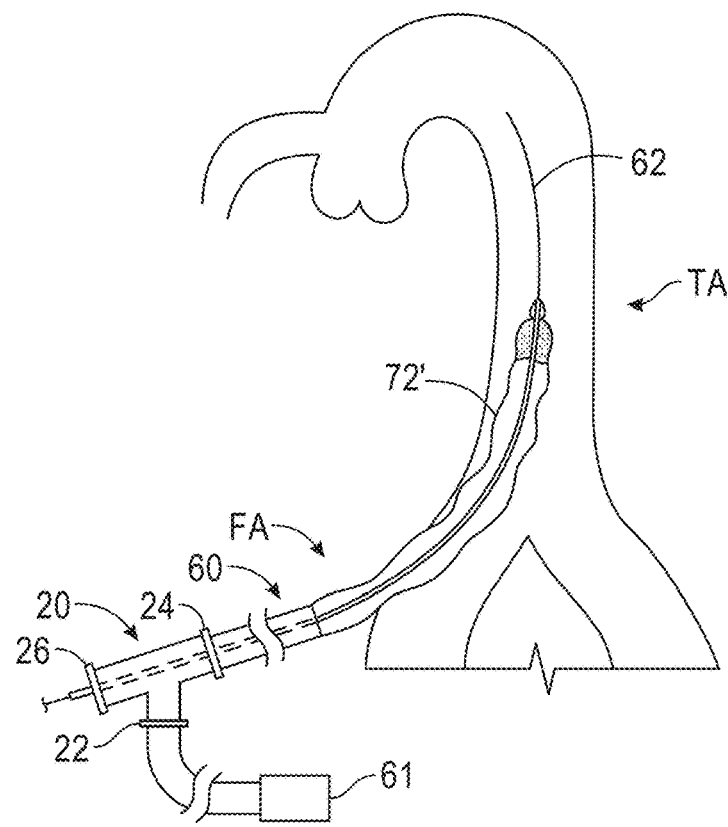
FIGS. 13A and 13B illustrate exemplary steps for improving perfusion during ECMO using the extension cannula of FIG. 11A.
Figure 13B:
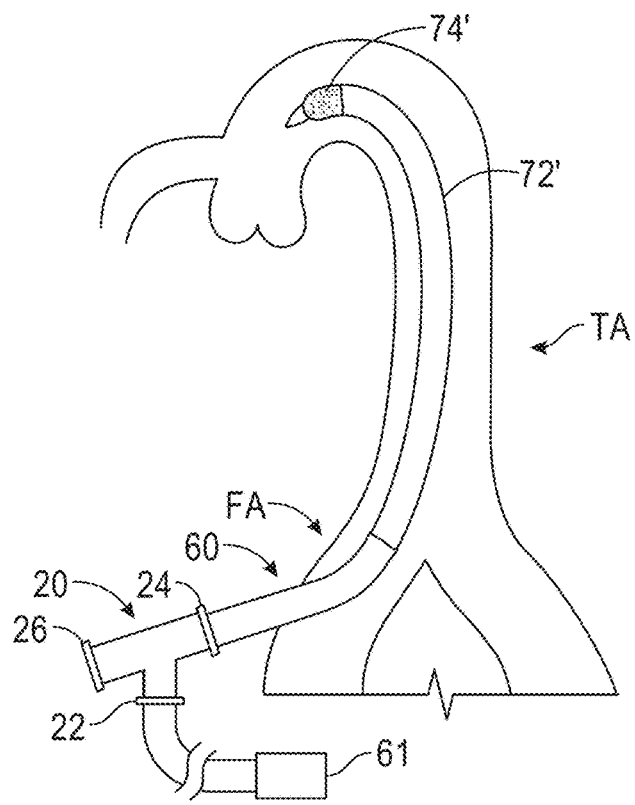

At step 101, the distal end of extension cannula 70', e.g., tip 78' of expandable conduit 72', is advanced over guidewire 62 via the lumen of hypotube 77', together with ECMO cannula 60 and in-line connector 20, as shown in FIG. 13A. Extension cannula 70', ECMO cannula 60, and in-line connector 20 are advanced until expandable conduit 72' is positioned at the desired central location within the patient's vasculature at step 102, and ECMO cannula 60 is positioned within the patient's femoral artery FA, as shown in FIG. 13B. At step 103, oxygenated blood may be perfused from ECMO machine 61 through the lumen of expandable conduit 72' via in-line connector 20 and ECMO cannula 60, thereby causing expandable conduit 72' to fully expanded within the patient's vasculature as shown in FIG. 13B, to the central location within the patient's vasculature, e.g., within the ascending aorta or in the vicinity of the aortic arch, via pores 74' at the distal region of expandable conduit 72'. As will be understood by a person of ordinary skill in the art, pores 74' of expandable conduit 72' may be positioned within the descending aorta, e.g., the portion of the descending aorta approaching the level of the diaphragm from beneath the thoracic cavity or the portion of the descending aorta above the diaphragm. When the ECMO therapy is complete, at step 104, the ECMO machine may be turned off, such that blood no longer flows through expandable conduit 72', thereby causing expandable conduit 72' to return to a semi-collapsed state, and at step 105, extension cannula 70' and ECMO cannula 60 may be removed from the patient.

Figure 14A:
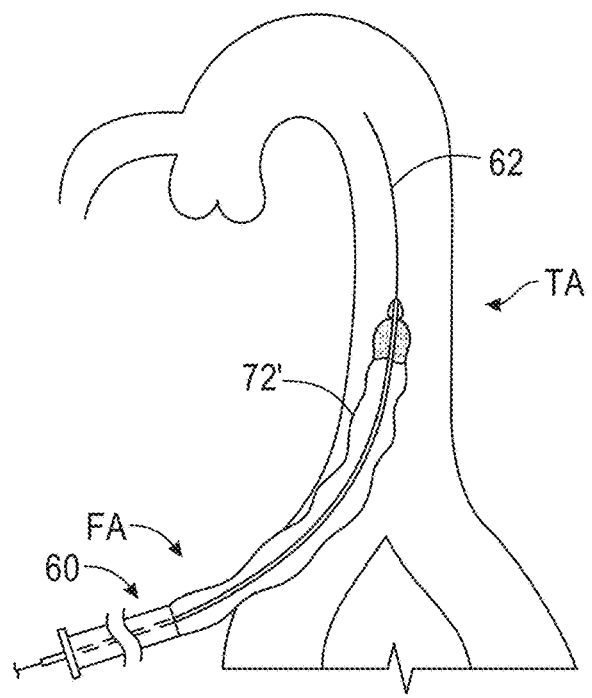
FIGS. 14A and 14B illustrate exemplary steps for improving perfusion during ECMO using the extension cannula of FIG. 11B.
Figure 14B:
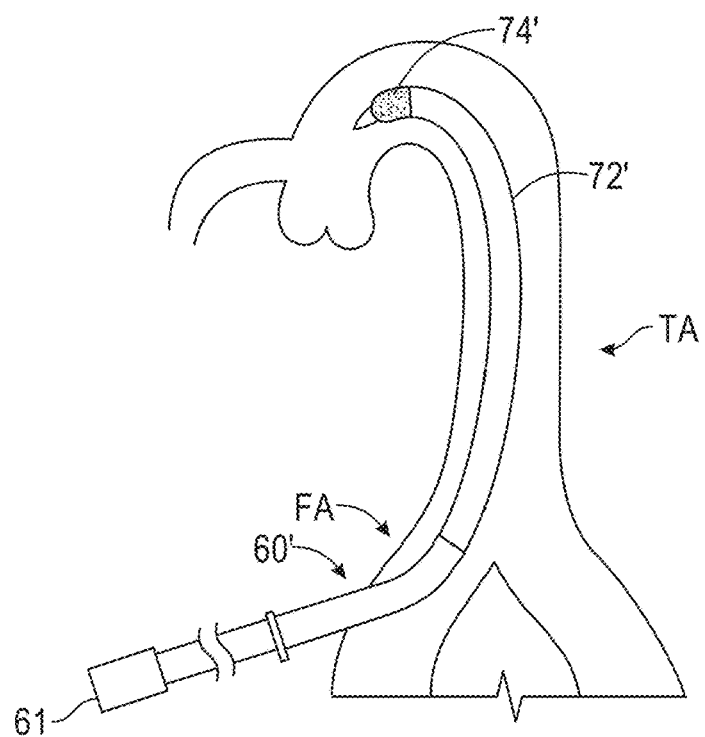

Referring now to FIGS. 14A and 14B, exemplary steps for improving perfusion during ECMO using the extension cannula of FIG. 11B is provided. Specifically, method steps 101-105 of FIG. 12 described above may be used to deliver extension cannula 70' for improving perfusion during ECMO, without use of an in-line connector. For example, at step 101 the distal end of extension cannula 70', e.g., tip 78' of expandable conduit 72', is advanced over guidewire 62 via the lumen of hypotube 77', together with ECMO cannula 60, as shown in FIG. 14A. Extension cannula 70' and ECMO cannula 60 are advanced until expandable conduit 72' is positioned at the desired central location within the patient's vasculature at step 102, and ECMO cannula 60 is positioned within the patient's femoral artery FA, as shown in FIG. 14B. Guidewire 62 may then be removed through the proximal end of ECMO cannula 60, and the proximal end of ECMO cannula 60 may then be coupled to ECMO machine 61.

As described above, at step 103, oxygenated blood may be perfused from ECMO machine 61 through the lumen of expandable conduit 72' via ECMO cannula 60, thereby causing expandable conduit 72' to fully expanded within the patient's vasculature as shown in FIG. 14B, to the central location within the patient's vasculature, e.g., within the ascending aorta or in the vicinity of the aortic arch, via pores 74' at the distal region of expandable conduit 72'. When the ECMO therapy is complete, at step 104, the ECMO machine may be turned off, such that blood no longer flows through expandable conduit 72', thereby causing expandable conduit 72' to return to a semi-collapsed state, and at step 105, extension cannula 70' and ECMO cannula 60 may be removed from the patient.

Figure 15A:
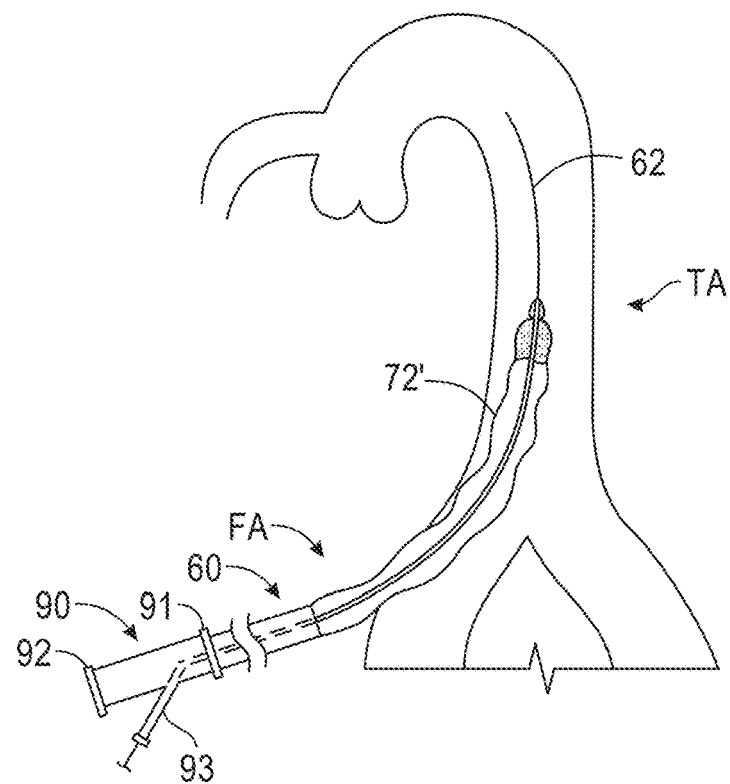
FIGS. 15A and 15B illustrate exemplary steps for improving perfusion during ECMO using the extension cannula of FIG. 11C.
Figure 15B:
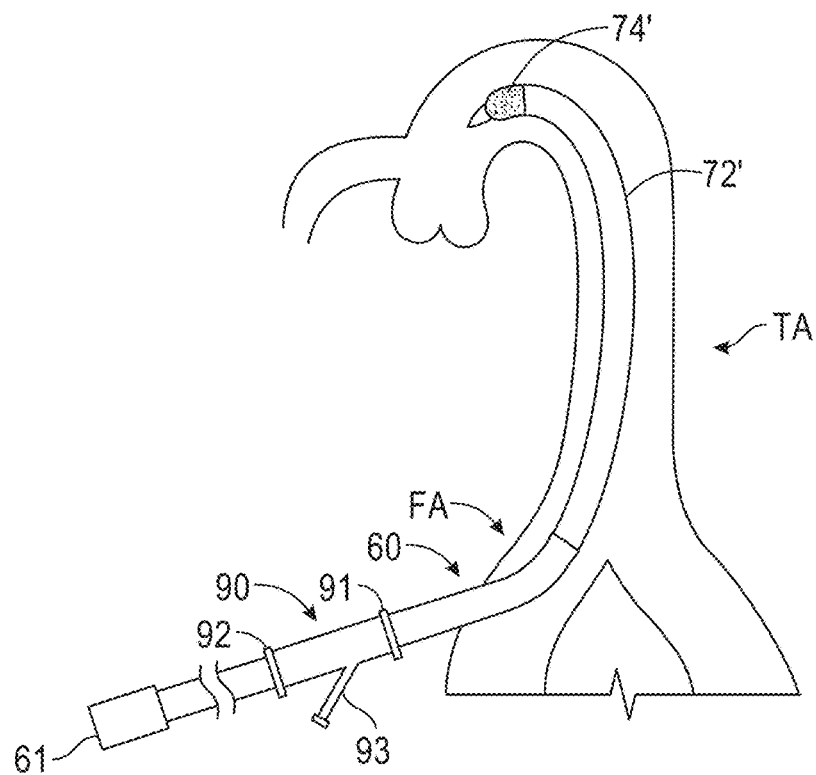

Referring now to FIGS. 15A and 15B, exemplary steps for improving perfusion during ECMO using the extension cannula of FIG. 11C is provided. Specifically, method steps 101-105 of FIG. 12 described above may be used to deliver extension cannula 70' having connector 90 coupled thereto for improving perfusion during ECMO. For example, at step 101 the distal end of extension cannula 70', e.g., tip 78' of expandable conduit 72', is advanced over guidewire 62 via the lumen of hypotube 77', together with ECMO cannula 60 and connector 90, as shown in FIG. 15A. Extension cannula 70' and ECMO cannula 60 are advanced until expandable conduit 72' is positioned at the desired central location within the patient's vasculature at step 102, and ECMO cannula 60 is positioned within the patient's femoral artery FA, such that guidewire 62 extends out of sidearm 93. Guidewire 62 may then be removed through sidearm 93. A stylet may then be inserted through sidearm 93 and hypotube 77', e.g., until the end of the stylet is adjacent to tip 78' of extension cannula 70', to thereby prevent blood from entering hypotube 77' and clotting therein during operation. Alternatively, an end cap may be coupled to sidearm 93. Inlet 92 of connector 90 may then be coupled to ECMO machine 61, as shown in FIG. 15B.

As described above, at step 103, oxygenated blood may be perfused from ECMO machine 61 through the lumen of expandable conduit 72' via connector 90 and ECMO cannula 60, thereby causing expandable conduit 72' to fully expanded within the patient's vasculature as shown in FIG. 15B, to the central location within the patient's vasculature, e.g., within the ascending aorta or in the vicinity of the aortic arch, via pores 74' at the distal region of expandable conduit 72'. When the ECMO therapy is complete, at step 104, the ECMO machine may be turned off, such that blood no longer flows through expandable conduit 72', thereby causing expandable conduit 72' to return to a semi-collapsed state. The stylet may then be removed from sidearm 93 and hypotube 77', guidewire 62 may be reinserted through sidearm 93 and hypotube 77'. At step 105, extension cannula 70' and ECMO cannula 60 may be removed from the patient, e.g., over guidewire 62. Existing long venous cannulas do not have a proximal side-connecting Luer lock, and thus, if such long venous cannulas were to be used in the arterial position, it would not provide antegrade perfusion of the leg. In contrast, existing arterial cannulas may include a proximal side-connecting Luer lock; however, such arterial cannulas are shorter than the existing long venous cannulas. Accordingly, the custom built extension cannulas described herein provide a proximal side connecting Luer lock on a long arterial cannula.

Figure 16A:
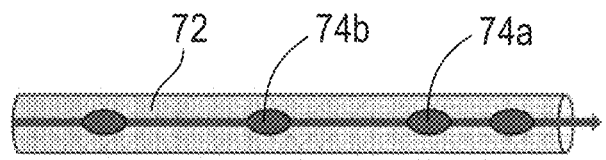
FIG. 16A to 16C illustrate various arrangements of the multiplicity of pores of the extension cannula in accordance with the principles of the present invention.
Figure 16B:
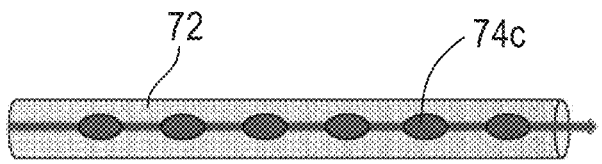
Figure 16C:
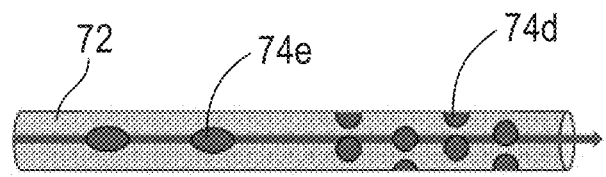

Referring now to FIGS. 16A to 16C, the extension cannulas described herein may include various arrangements and configurations of pores disposed on at least the distal region of the expandable conduit, the pores sized and shaped to permit blood flow therethrough to thereby avoid blood stasis or clotting along the length of the cannula and to more evenly distribute flow in the aorta, thereby also avoiding loading of the left ventricle. As shown in FIG. 16A, the plurality of pores may include first plurality of pores 74a and second plurality of pores 74b, which may have a longitudinally extending shape, e.g., oval shape. Moreover, pores 74a and pores 74b may be arranged laterally along the length of at least the distal region of the expandable conduit, e.g., expandable conduit 72, such that pores 74b are proximal to pores 74a. In addition, pores 74a may be disposed spatially apart from each other along the expandable conduit by a distance that is less than the distance pores 74b are spatially disposed apart by along the expandable conduit.

As shown in FIG. 16B, the plurality of pores may include pores 74c, which may have a longitudinally extending shape, e.g., oval shape, and may be equally spatially disposed from each other along the length of at least the distal region of the expandable conduit, e.g., expandable conduit 72.

As shown in FIG. 16C the plurality of pores may include first plurality of pores 74d and second plurality of pores 74e. Pores 74d may have a circular shape, and may be disposed circumferentially about at least the distal region of the expandable conduit, e.g., expandable conduit 72. As shown in FIG. 16C, plurality of pores 74d may include multiple rows of circumferentially disposed pores. Although FIG. 16C illustrates four rows of circumferentially disposed pores 74d, as will be understood by a person having ordinary skill in the art, pores 74d may include less or more than four rows of circumferentially disposed pores. Moreover, pores 74e may include multiple pores arranged laterally along the length of at least the distal region of the expandable conduit. As shown in FIG. 16C, pores 74e may be proximal to pores 74d. As will be understood by a person having ordinary skill in the art, the plurality of pores described herein may have any combination of the arrangements and configurations described above. For example, the laterally disposed pores may have a circular shape, and the circumferentially disposed pores may have a longitudinally extending shape, or any combination thereof.

Figure 17:
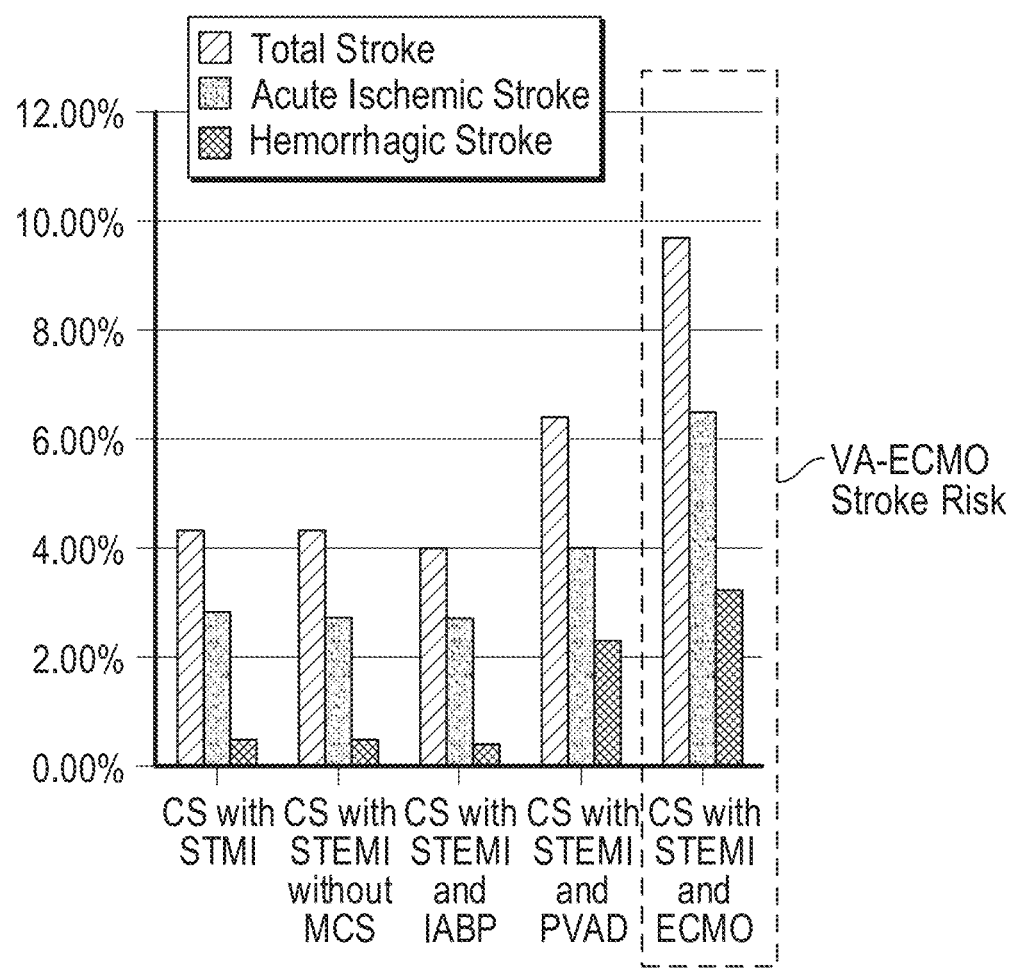
FIG. 17 is a graph illustrating VA-ECMO stroke risk.

FIG. 17 is a graph illustrating stroke risk for patient's undergoing various therapies include VA-ECMO. As shown, a patient undergoing VA-ECMO generally has the highest risk of total stroke, e.g., acute ischemic stroke and hemorrhagic stroke. In accordance with the principles of the present invention, the systems and methods described herein are expected to provide oxygenated blood to the cerebral vasculature and provide antegrade flow from the outlet of the self-expanding conduit. This in turn is expected to reduce the risk of ischemic stroke and reduce blood flow rates and pressures that could induce kidney injury.

Figure 18:
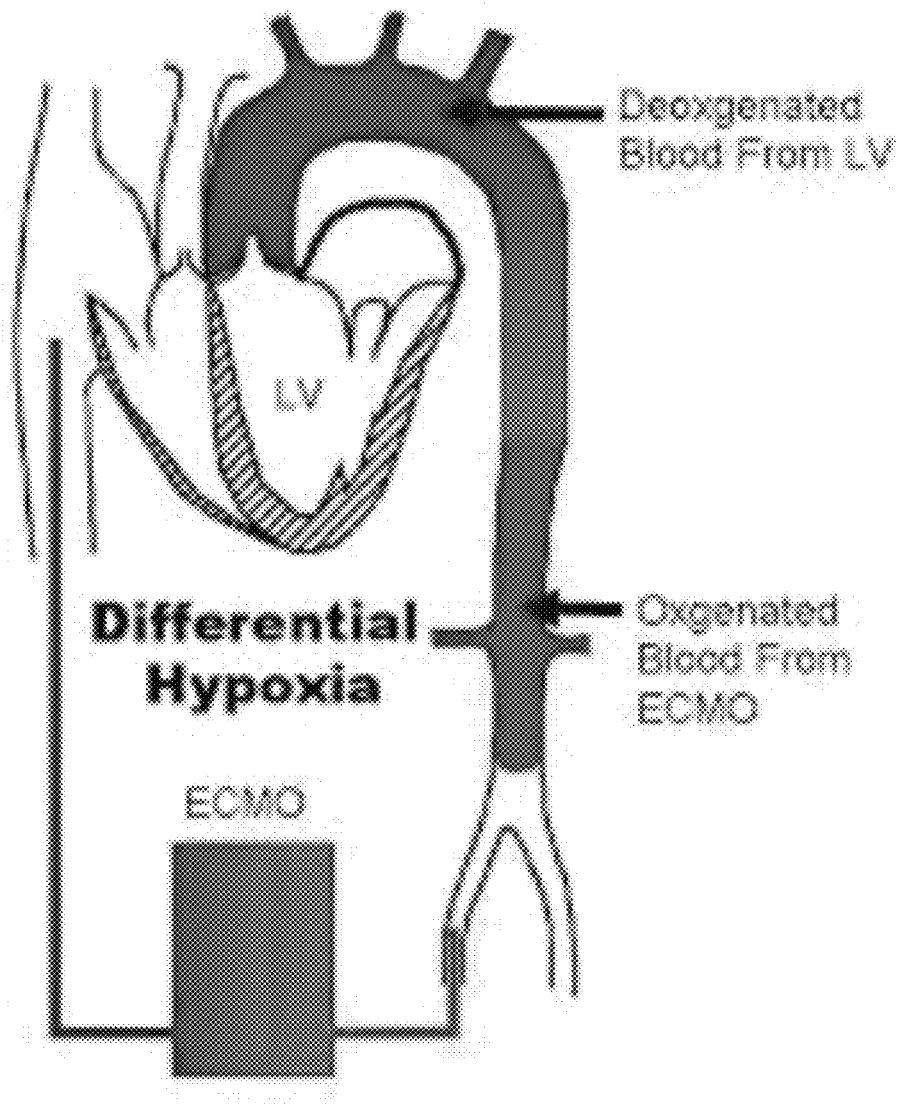
FIG. 18 depicts north-south syndrome in a patient on ECMO.

With respect to FIG. 18, a further expected benefit of the system and method of the present invention is described. FIG. 18 illustrates a situation referred to as "north-south syndrome" that may arise in a patient on ECMO, particularly patients having compromised lung function. In such cases, although the heat is beating, the blood returned to circulation by the left ventricle may be poorly oxygenated. In this case, if a conventional ECMO return catheter is employed, oxygenated blood reperfused into the patient mixes with the antegrade flow of deoxygenated blood from the lungs, resulting in differential hypoxia. Because the extension cannula of the present invention is designed to deliver blood into the ascending aorta, the system and methods of the present invention are expected to significantly ameliorate the effect of compromised lung function and reduce the occurrence and severity of north-south syndrome.

Figure 19:
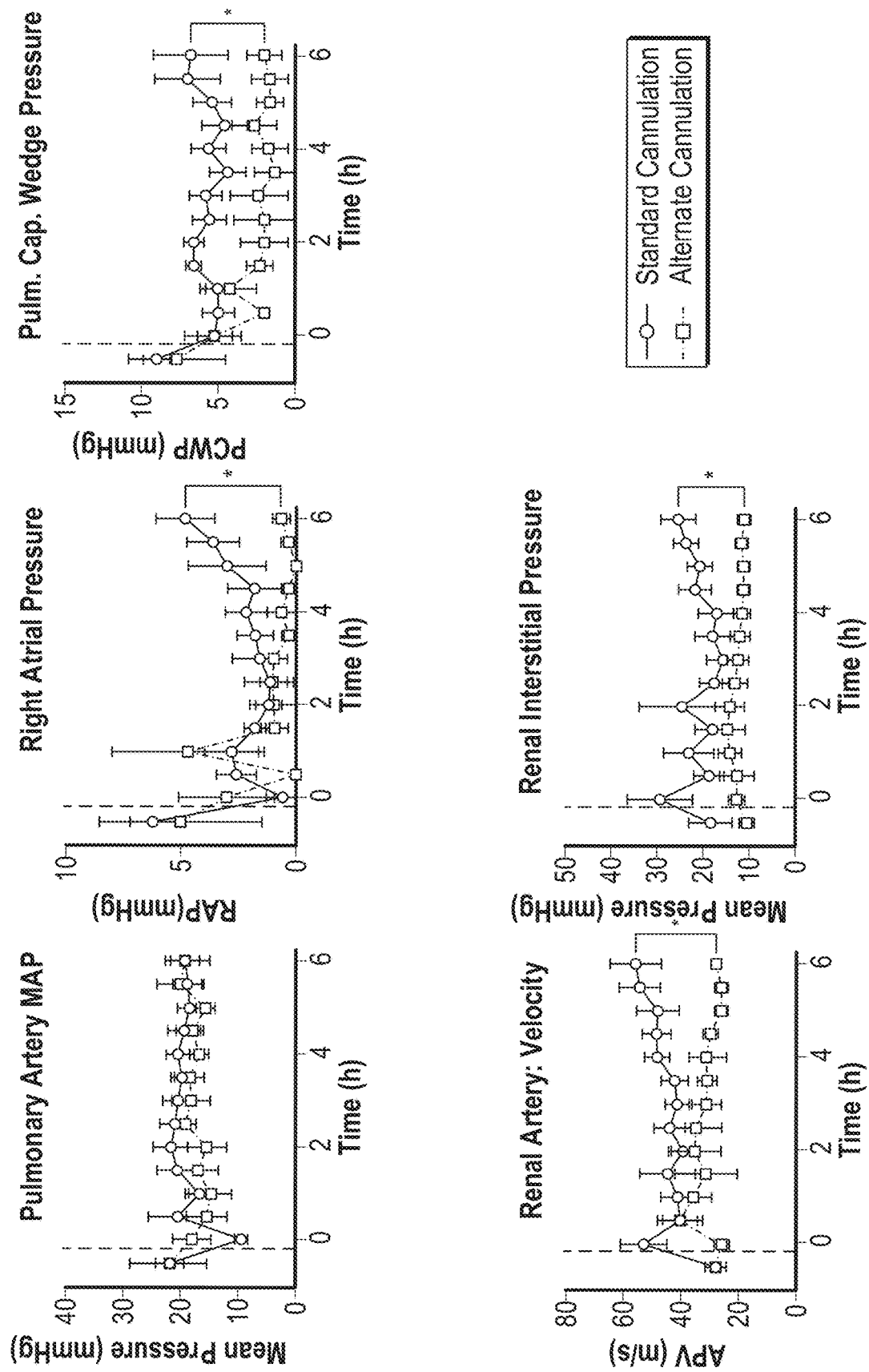
FIG. 19 is a series of graphs illustrating various parameters for standard conventional ECMO cannulation compared to those achieved using alternate cannulation (delivery of blood to the thoracic aorta) in accordance with the principles of the present invention.
Figure 20:
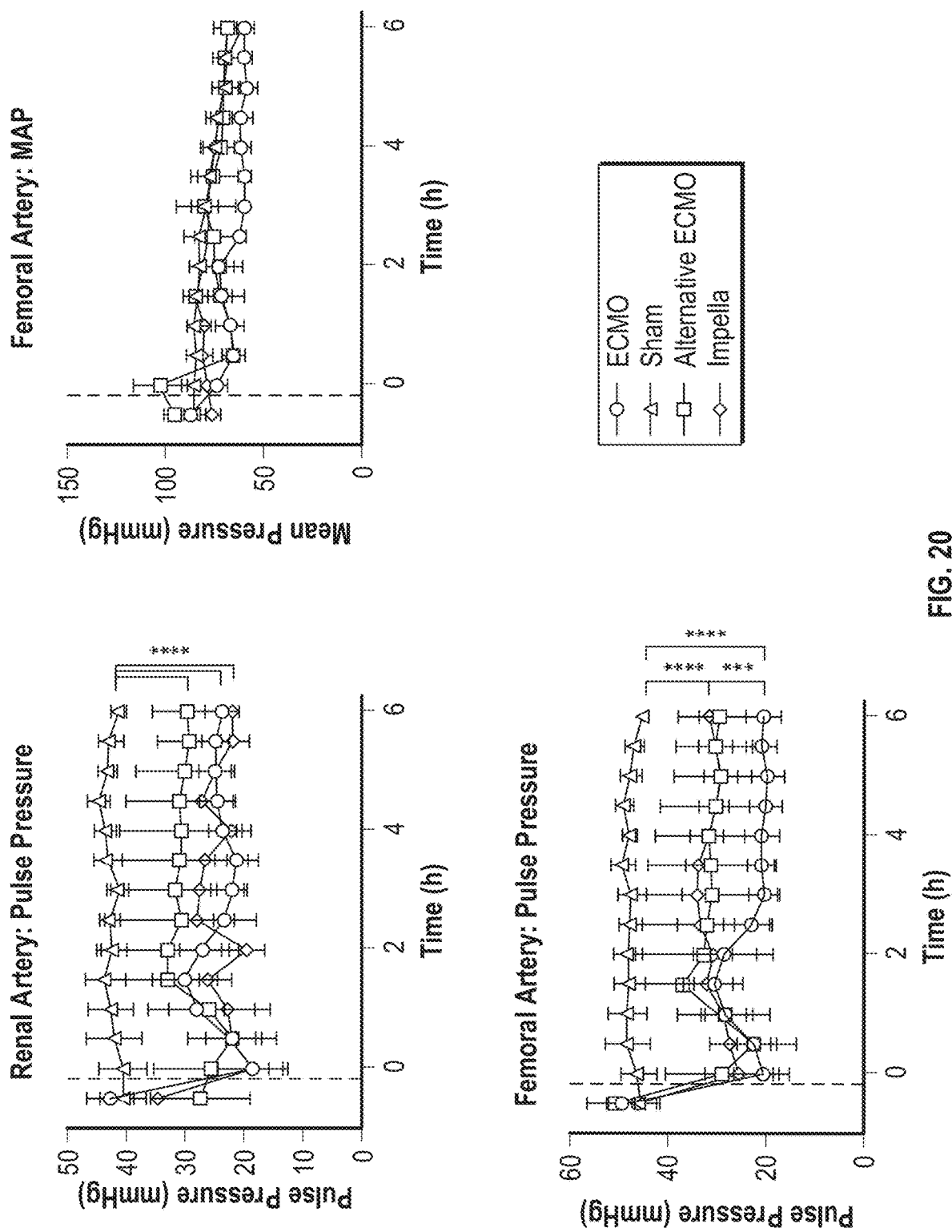
FIG. 20 is a series of graphs illustrating various parameters resulting from use of standard conventional ECMO cannulation, an Impella pump, and an exemplary system of the present invention.

Preclinical data from experiments utilizing an extension cannula constructed in accordance with the principles of the present invention demonstrate superior performance compared to conventional ECMO return cannulas. FIG. 19 is a series of graphs comparing various parameters measured during standard VA-ECMO cannulation and with use of the extension cannula of the present invention (defined as "Alternate Cannulation" in FIG. 19). In particular, the alternate cannulation of the present invention results in reduced pulmonary artery mean arterial pressure (MAP), reduced right arterial pressure, reduced pulmonary capillary wedge pressure, reduced renal arterial flow velocity, and reduced renal interstitial pressure (organ pressure), compared to standard VA-ECMO cannulation. These findings suggest that placement of an extension cannula may reduce cardiac, lung, and kidney injury when compared to standard VA-ECMO alone. Specifically, this data shows reduced heart pressures (right atrial pressure and pulmonary capillary wedge pressure), normal renal artery velocity, and normal renal interstitial (organ) pressures with alternate cannulation as opposed to standard cannulation (delivery of blood to the femoral artery). Further, as shown in FIG. 20, the alternate cannulation of the present invention provides increased pulsatile arterial flow in the renal artery and the femoral artery compared to standard VA-ECMO cannulation. Compared to sham operated animals, standard femoral cannulation ECMO reduces renal and femoral artery pulse pressure, e.g., pulsatility. Compared to standard cannulation, alternative cannulation (delivery of blood to the thoracic aorta) has increased renal and femoral artery pulse pressure, e.g., pulsatility. Improved physiologic pulsatility is further associated with less injury.

Figure 21:
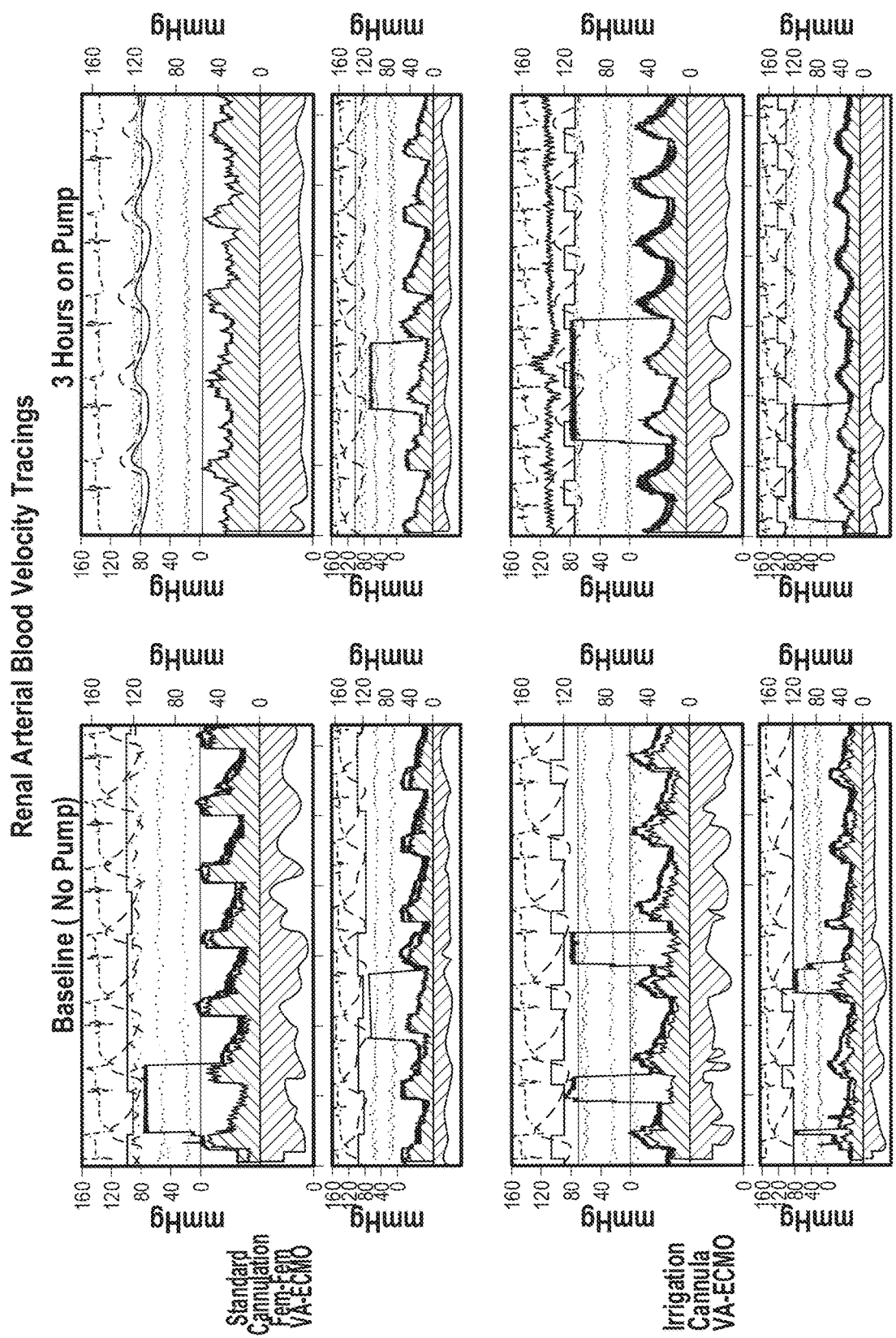
FIG. 21 is a series of graphs representing renal arterial blood velocity obtained for standard conventional ECMO cannulation and an exemplary alternate (irrigation) cannulation system of the present invention.
Figure 22:
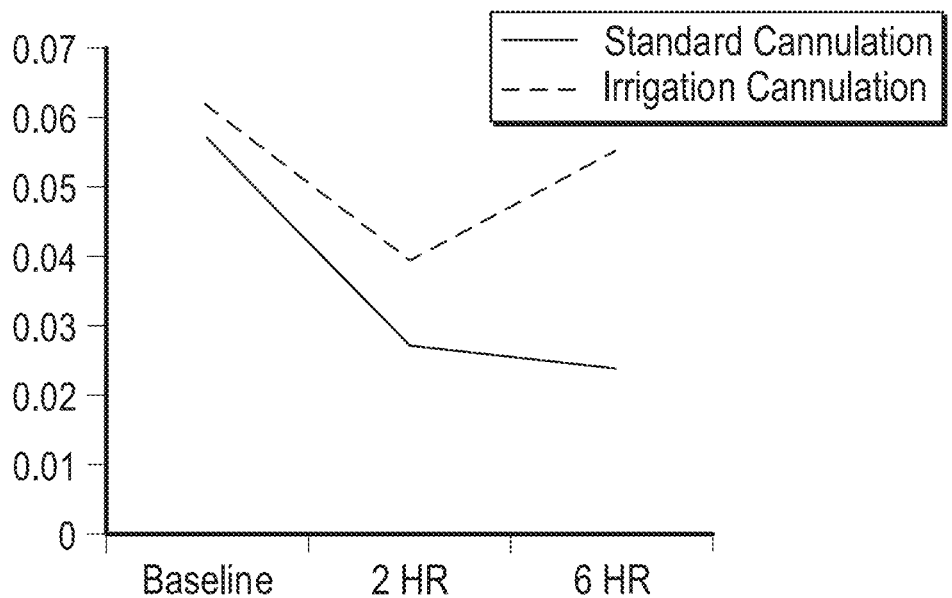
FIG. 22 are graphs illustrating renal arterial pulsatility and renal arterial microvascular resistance for standard conventional ECMO cannulation and an exemplary alternate cannulation system of the present invention.
Figure 22:
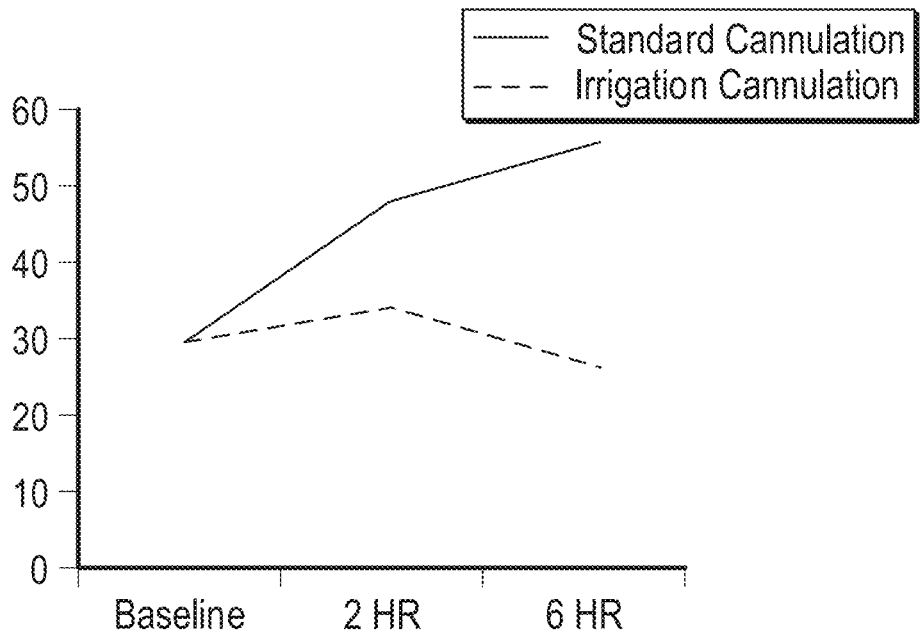
Figure 23:
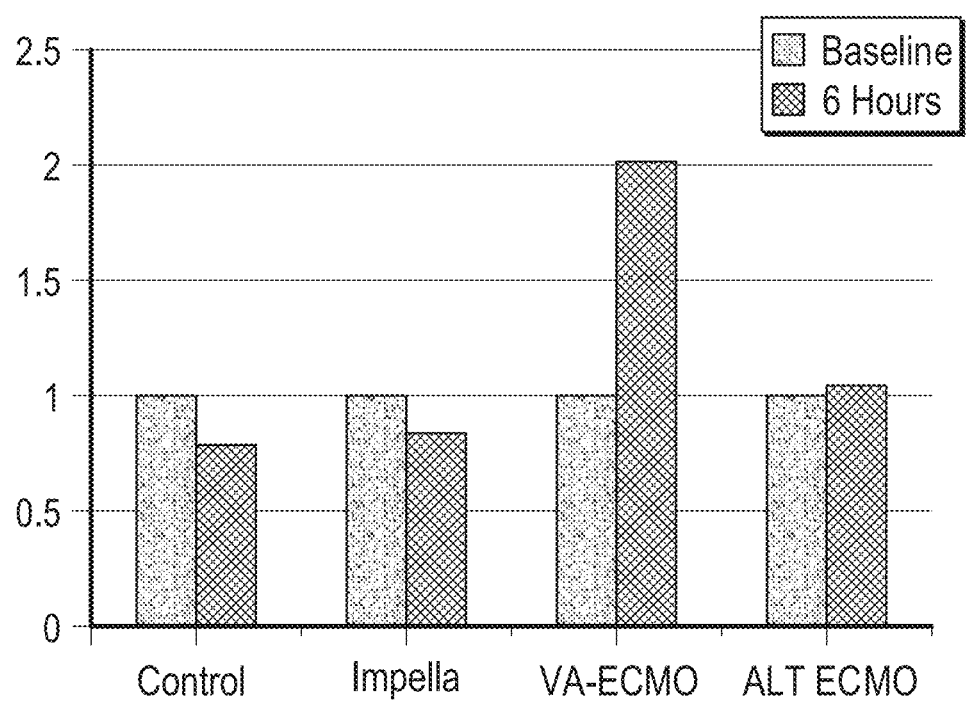
FIG. 23 is a graph showing urinary levels of kidney injury molecules associated with use of standard conventional ECMO cannulation and an exemplary alternate cannulation system of the present invention.

FIGS. 21 and 22 provide further comparisons of use of the alternate cannulation of the present invention compared to standard ECMO cannulation, demonstrating improved renal arty pulsatility and reduced microvascular resistance in the kidney. Regarding FIG. 21, compared to standard cannulation, alternate (irrigation) cannulation preserves pulsatility in the renal artery after three hours of pumping. Regarding FIG. 22, compared to standard cannulation, alternate (irrigation) cannulation preserves pulsatility (renal resistance index) and reduces renal arterial microvascular resistance in the renal artery after two and six hours of pumping. Similarly, FIG. 23 demonstrates that the alternate cannulation of the present invention ("ALT ECMO") results in lower levels of kidney injury molecule 1 (KIM-1) in the urine, indicating less kidney injury suffered by the patient. Compared to standard VA-ECMO, ALT ECMO is associated with lower (normal) levels of kidney injury marker in the urine.

Figure 24A:
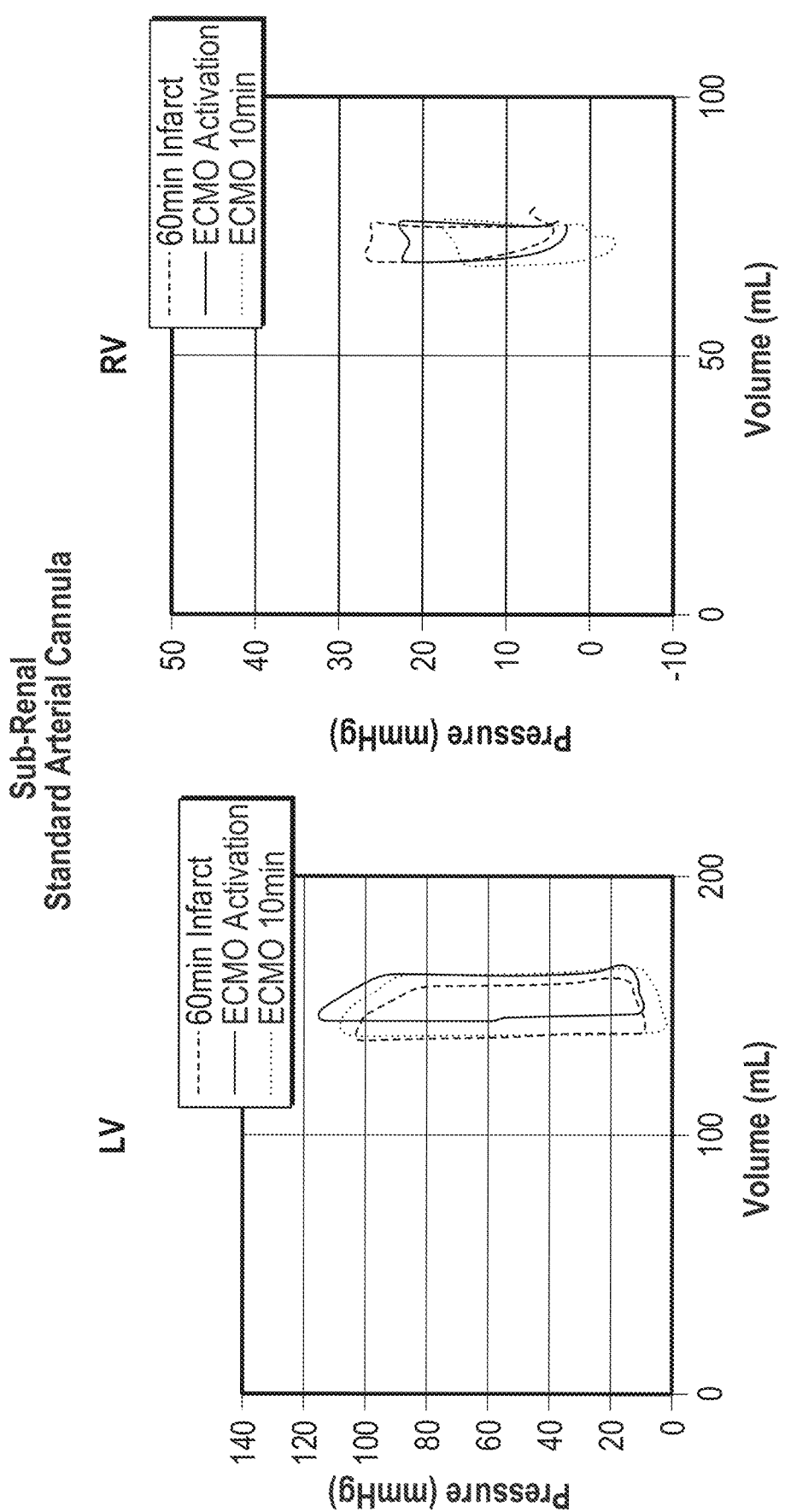
FIG. 24A illustrates left ventricular and right ventricular response during conventional ECMO cannulation.
Figure 24B:
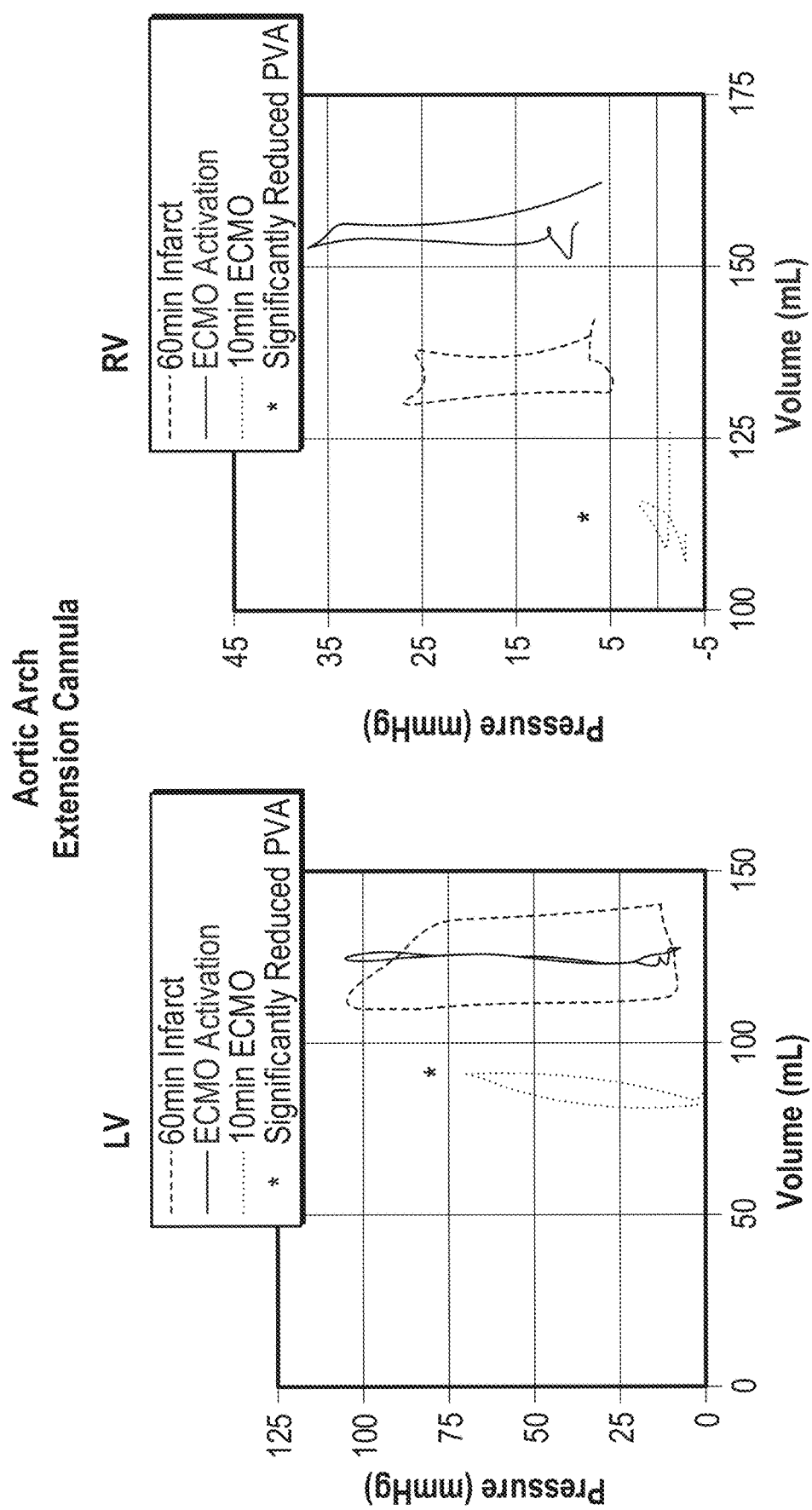
FIG. 24B illustrates left ventricular and right ventricular response during ECMO using the extension cannula of the present invention.

FIGS. 24A and 24B provide a further comparison of use of the alternate cannulation of the present invention compared to standard ECMO cannulation, demonstrating significant and unexpected reduction in both left and right ventricular workload. FIG. 24A is a graph of measured Pressure versus Volume that includes traces for the left and right ventricles at 60-minutes post-infarct, immediately after commencement of arterial ECMO cannulation within the femoral artery at a standard sub-renal outlet location, and after ten minutes of standard arterial ECMO cannulation. The area within the respective Pressure versus Volume loops, referred to as "PVA", is a measure of the work performed by the heart during the cardiac cycle. The graphs of FIG. 24A show that the pressure/volume loops for the left ventricle (LV) are substantially unchanged by ECMO reperfusion. Similarly, the right ventricle (RV) also does not experience a significant reduction in workload after standard arterial ECMO cannulation. By way of possible explanation, but without intending to be limiting, it is postulated that the left and right ventricular workload is substantially unchanged because introduction of continuous high flow below the renal arteries causes the blood column in the descending aorta to stagnate, which in turn causes the LV pressures to remain high. Thus, it is believed that the heart must continue working to overcome the resistance to antegrade flow created by the ECMO-infused blood. Accordingly, during standard ECMO cannulation, femoral delivery of arterial blood pressurizes the entire aorta, thereby increasing the load against which the native heart must pump.

In contrast, as shown in FIG. 24B, when the extension cannula of the present invention is deployed to extend the ECMO outlet within the aortic arch, both the left ventricle (LV) and the right ventricle (RV) experience a significant reduction in workload after commencement of ECMO activation, and thereafter, compared to standard arterial ECMO cannulation in FIG. 24A. Specifically, the pressure/volume loops for the left ventricle (LV) significantly decrease, and the pressure/volume loops for the right ventricle (RV) decreases even more, thus illustrating the effectiveness of the extension cannula of the present invention in reducing cardiac workload during ECMO reperfusion. Again by way of explanation, but without intending to be limiting, it is postulated that the significant decrease in left and right ventricular workload is due to the delivery of blood into the aortic arch, which enhances antegrade blood flow to the descending aorta as well as the arteries adjoining the aortic arch. Thus, the resulting forward flow, which fully develops during the 10 minutes after commencement of ECMO reperfusion, unloads the LV, thereby causing lesser cardiac output, but at much lower pressure. Moreover, it is believed that the reduced load in the LV may assist blood transiting the lungs, further reducing RV workload. Accordingly, by delivering blood in the aortic arch, the arterial tree is not pressurized, thereby avoiding increased pressure load that the heart might otherwise have to work against, which allows for more effective venous drainage of the heart, and thus reduced RV and LV volumes, without the cost of increasing ventricular pressure.

Figure 25:
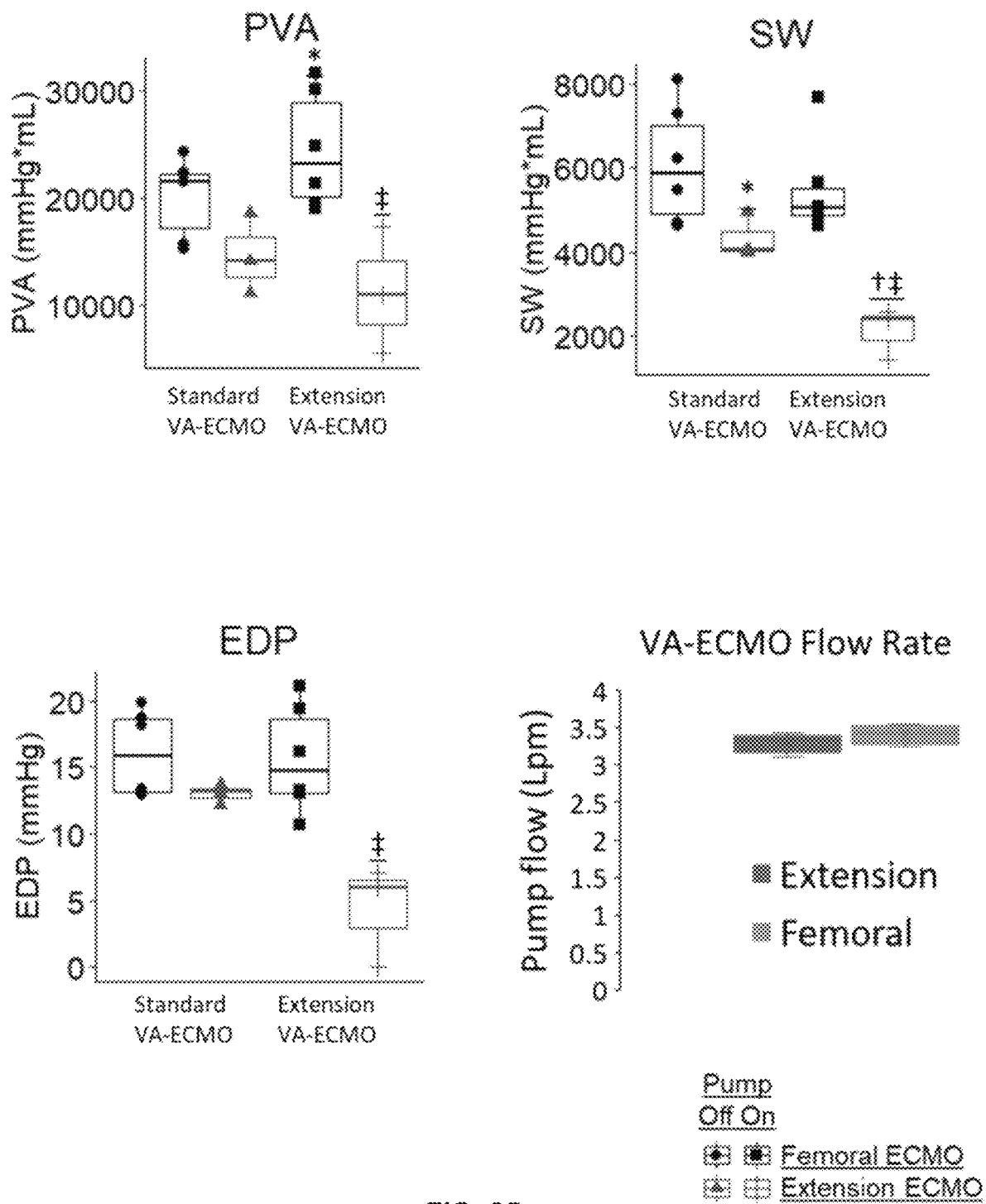
FIG. 25 are graphs illustrating pressure volume area (PVA), stroke work (SW), and end-diastolic pressure (EDP) associated with use of standard conventional ECMO cannulation and an exemplary alternate cannulation system of the present invention.

FIG. 25 are graphs illustrating pressure volume area (PVA), stroke work (SW), and end-diastolic pressure (EDP) associated with use of standard conventional VA-ECMO cannulation and the alternate extension cannulation of the present invention. As shown in FIG. 25, despite equivalent rates of flow through the VA-ECMO circuits (bottom right), compared with standard conventional VA-ECMO, use of the alternate extension cannulation of the present invention reduces PVA, SW, and EDP, thereby evidencing that the alternate extension cannulation of the present invention reduces cardiac workflow.

Figure 26B:
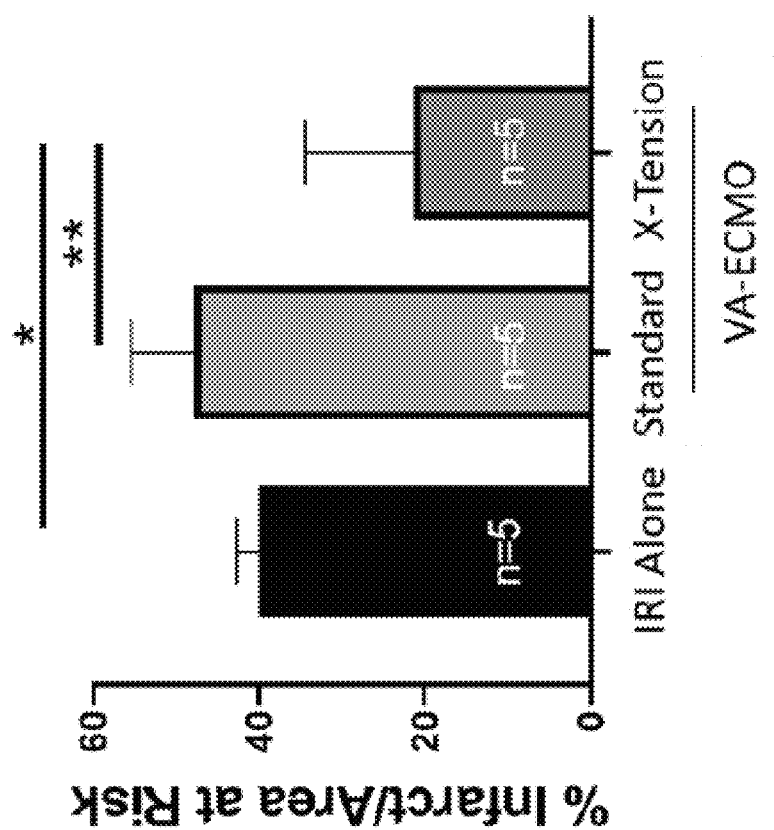
FIG. 26B is a graph show infarct size associated with standard ischemia and reperfusion injury (IRI) and use of standard conventional ECMO cannulation and an exemplary alternate cannulation system of the present invention.
Figure 26A:
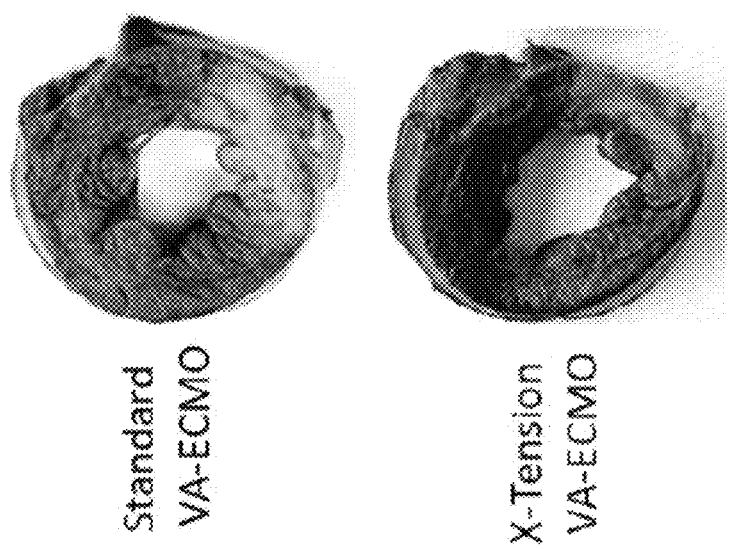
FIG. 26A illustrates infarct size associated with use of standard conventional ECMO cannulation and an exemplary alternate cannulation system of the present invention.

FIG. 26A illustrates infarct size associated with use of standard conventional ECMO cannulation and the alternate cannulation of the present invention. As shown in FIG. 26B, infarct size associated with use of the alternate extension cannulation of the present invention is much lower than the infarct sizes associated with standard ischemia and reperfusion injury (IRI) and with use of standard conventional ECMO cannulation.

Figure 27:
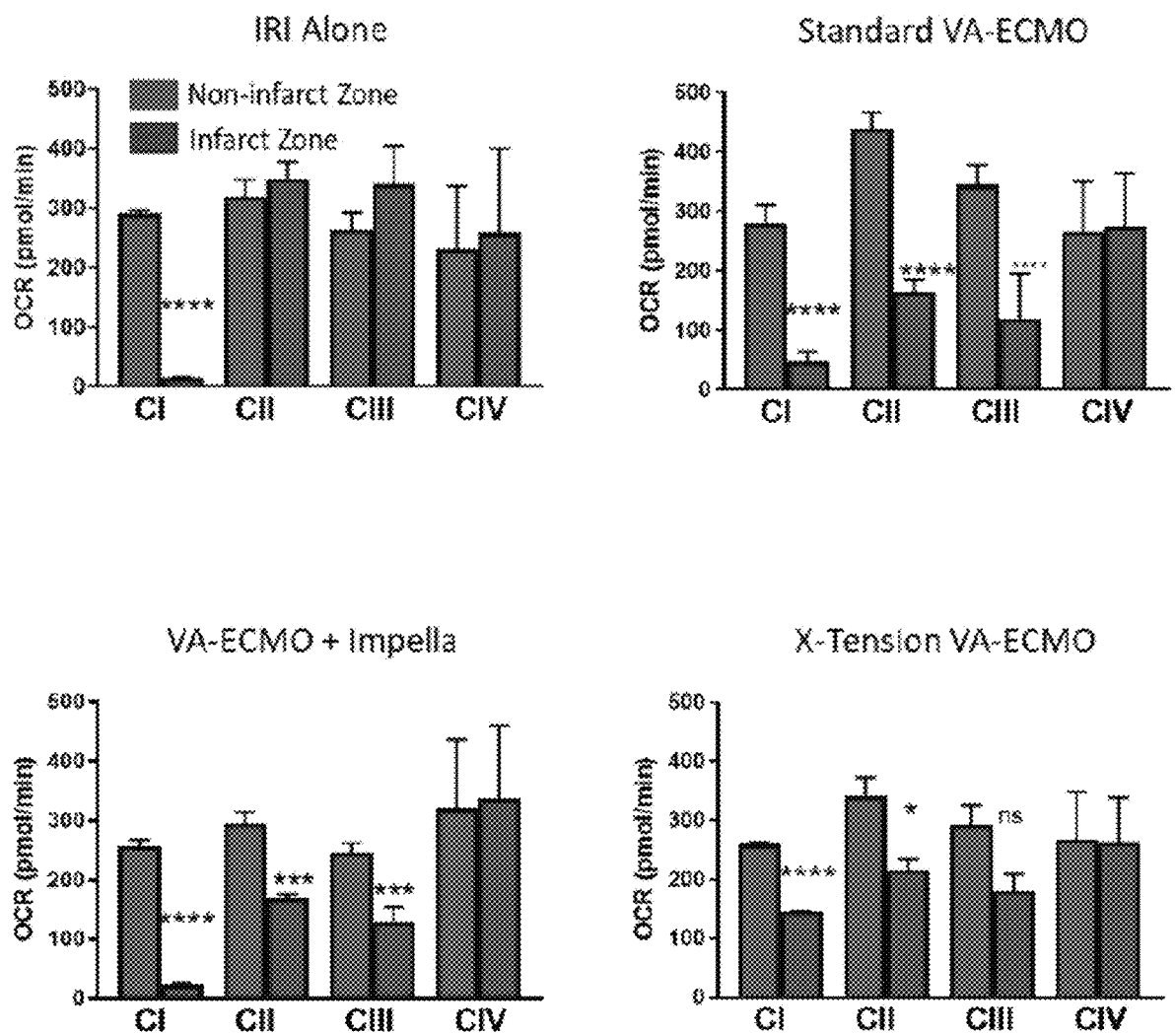
FIG. 27 are graphs illustrating oxygen consumption rate (OCR) associated with standard ischemia and reperfusion injury (IRI) and use of standard conventional ECMO cannulation, with and without an Impella, and an exemplary alternate cannulation system of the present invention.

FIG. 27 are graphs illustrating oxygen consumption rate (OCR) associated with standard ischemia and reperfusion injury (IRI) and use of standard conventional ECMO cannulation, with and without an Impella device, and the alternate extension cannulation of the present invention, which is indicative of the function of the mitochondria. Mitochondria are known as the "powerhouse" of the cell, generating ATP via oxidative phosphorylation (OXPHOS) complexes, which are present in the inner membrane of mitochondria. These complexes are known as NADH: ubiquinone oxidoreductase (complex I), succinate dehydrogenase (complex II), ubiquinol—cytochrome c oxidoreductase (complex III, or cytochrome bc1 complex), cytochrome c oxidase (complex IV), and ATP synthase (complex V).

Complex I (CI) is the largest and most complicated component of the respiratory chain. Using the bovine heart as the model system, previous work has characterized all the complex I subunits and cloned the encoding genes. Mitochondrial CI accounts for 40% of proton motive force required to maintain ATP synthase in the electron transport chain (ETC). In a recent study, it was shown that reducing left heart workload with a mechanical pump can reduce myocardial damage and preserve mitochondrial CI function. See, e.g., Lija Swain, PhD, et al., Transvalvular Ventricular Unloading before Reperfusion in Acute Myocardial Infarction, Journal of the American College of Cardiology, Vol. 76, No. 6, 2020. The study further found that use of VA-ECMO during a heart attack fails to reduce left heart workload and increases myocardial damage, and significantly reduces mitochondrial CI function. This effect of VA-ECMO cannot be rescued by placing an unloading pump after VA-ECMO has been initiated. The study illustrated that using the alternate extension cannulation of the present invention with VA-ECMO reduces left heart workload, reduces myocardial damage, and improves function of mitochondrial CI.

Figure 28:
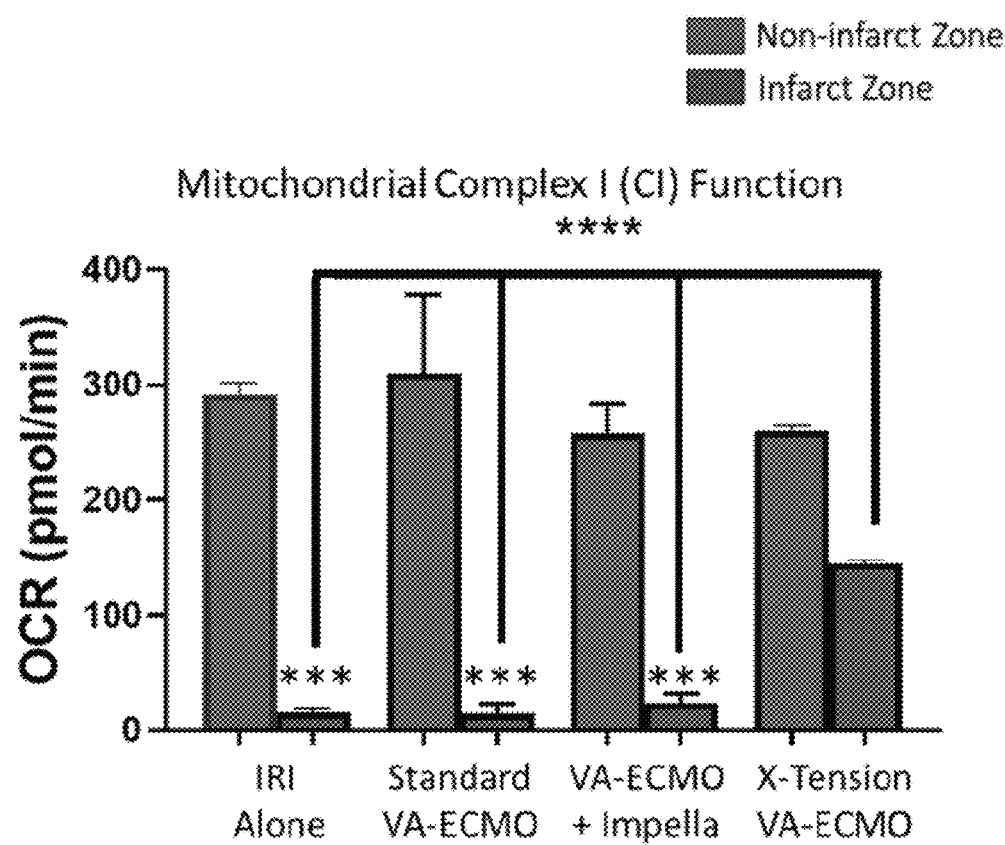
FIG. 28 is a graph illustrating oxygen consumption rate (OCR) associated with standard ischemia and reperfusion injury (IRI) and use of standard conventional ECMO cannulation, with and without an Impella, and an exemplary alternate cannulation system of the present invention for mitochondrial complex I (CI) function.

For example, as shown in FIG. 27, compared with IRI alone, standard conventional VA-ECMO alone, and standard conventional VA-ECMO with an Impella device, use of the alternate extension cannulation of the present invention with VA-ECMO preserves function of mitochondrial CI, as measured by oxygen consumption rate (OCR), which when impaired, contributes to myocardial damage and infarct size. Moreover, as shown in FIG. 28, compared to the non-infarct zone, mitochondrial CI function is significantly reduced in the infarct zone after IRI alone, standard conventional VA-ECMO alone, and standard conventional VA-ECMO with an Impella device. In contrast, mitochondrial CI function is significantly higher in the infarct zone after treatment using the alternate extension cannulation of the present invention with VA-ECMO. These data identify for the first time that the point of delivery for arterial blood returning from VA-ECMO promotes a cardio-protective effect on the heart, which has implications for any patient receiving VA-ECMO and especially for patients receiving VA-ECMO who are having a heart attack or heart injury.

While various illustrative embodiments of the invention are described above, it will be apparent to one skilled in the art that various changes and modifications may be made therein without departing from the invention. For example, as will be understood by a person having ordinary skill in the art, the systems and methods described herein are not limited for use with a VA-ECMO system. For example, the inventive extension cannula may also be used with, e.g., a venous-venous ECMO (VV-ECMO) system. Moreover, the extension cannulas and in-line connectors described herein may be used in conjunction with a conventional ECMO drainage catheter such that the extension cannula extends from the drainage catheter at the femoral vein to within the pulmonary artery or right ventricle of the patient, thereby permitting blood to be pumped directly out of the heart, effectively functioning as a ventricular assist device. The appended claims are intended to cover all such changes and modifications that fall within the true scope of the invention.

What is claimed:

1. An extension cannula for use with an ECMO return cannula having an inlet, an outlet, and a lumen configured to define a blood flow path, the extension cannula comprising:
    an elongated shaft having a proximal end and a distal region;
    a flexible conduit coupled to the distal region of the elongated shaft and having a proximal end, a distal end, and an internal lumen, the proximal end configured to engage the outlet of the ECMO return cannula to form a continuation of the blood flow path through the lumen of the ECMO return cannula, the flexible conduit configured to transition between a collapsed insertion state and an expanded deployed state when in communication with a blood flow from the ECMO machine through the internal lumen; and
    a connection structure configured to couple the flexible conduit to the distal region of the elongated shaft,
    wherein the elongated shaft is configured to advance the flexible conduit to locate the distal end beyond the patient's renal vessels,
    wherein the flexible conduit has a length selected so that when the extension cannula is in the expanded deployed state, the proximal end is located within the outlet of the ECMO return cannula at a location proximal of the patient's renal vessels, and the distal end extends beyond the outlet of the ECMO return cannula and the patient's renal vessels, and
    wherein the elongated shaft is configured so that the blood flow path does not pass through the elongated shaft.

2. The extension cannula of claim 1, wherein the elongated shaft comprises a hypotube having a lumen configured to receive a guidewire therethrough.

3. The extension cannula of claim 1, wherein the flexible conduit comprises at least one of polyethylene, polyurethane, or nylon.

4. The extension cannula of claim 1, wherein the flexible conduit comprises a biocompatible fabric.

5. The extension cannula of claim 1, wherein the outlet of the flexible conduit comprises one or more pores disposed at a distal region of the flexible conduit.

6. The extension cannula of claim 1, wherein a distal end of the elongated shaft comprises a tip coupled to the distal end of the flexible conduit via the connection structure.

7. The extension cannula of claim 6, wherein the connection structure comprises one or more umbrella-like struts.

8. The extension cannula of claim 6, wherein the elongated shaft has a length selected so that the elongated shaft extends proximally from the tip through the internal lumen of the flexible conduit and beyond the proximal end of the flexible conduit.

9. The extension cannula of claim 1, wherein the proximal end of the flexible conduit is configured to engage the outlet of the ECMO return cannula by an anchoring stent.

10. The extension cannula of claim 9, wherein the anchoring stent is self-expandable.

11. The extension cannula of claim 1, wherein the proximal region of the flexible conduit is configured to be fixedly coupled to the ECMO return cannula within the outlet of the ECMO return cannula.

12. The extension cannula of claim 1, wherein the flexible conduit is configured to be inserted through the lumen of the ECMO return cannula in the collapsed insertion state using the elongated shaft, and to transition to the expanded deployed state when in communication with the blood flow from the ECMO machine.

13. The extension cannula of claim 1, wherein the elongated shaft is configured to advance the flexible conduit to position the proximal end of the flexible conduit within the outlet of the ECMO return cannula.

14. The extension cannula of claim 1, further comprising a sheath configured to be removably disposed over the flexible conduit to retain the flexible conduit in the collapsed insertion state.

15. An extension cannula system comprising:
the extension cannula of claim 1; and
an in-line connector configured to be coupled to the ECMO return cannula, the in-line connector having an inlet configured to be removably coupled to an outlet of an ECMO circuit, an outlet in fluid communication with the inlet and configured to be removably coupled to the ECMO return cannula, and a side arm having a lumen in fluid communication with a lumen of the elongated shaft, the lumens of the side arm and the elongated shaft sized and shaped to receive a guidewire therethrough.

16. A kit for use with an ECMO machine, the kit comprising:
a cannula comprising a proximal region having an inlet configured to be coupled to the ECMO machine, and an outlet configured to be disposed at a location within a patient's vasculature proximal of a patient's renal vessels; and
an extension cannula comprising:
a conduit comprising a flexible and collapsible tube having a proximal end, a distal end, a length extending therebetween, and a lumen in an expanded deployed state, the conduit configured to transition from a collapsed insertion state to the expanded deployed state when in communication with a blood flow from the ECMO machine; and
an elongated shaft having a distal region coupled to the distal end of the conduit, the elongated shaft configured to advance the conduit in the collapsed insertion state to locate the distal end beyond the patient's renal vessels,
wherein the length of the conduit is selected so that when the proximal end is located within the outlet at the location within the patient's vasculature proximal of the patient's renal vessels, the distal end extends beyond the patient's renal vessels, and the conduit transitions to the expanded deployed state in the presence of blood flow from the ECMO machine so that the lumen forms a continuation of a blood flow path through the cannula, and
wherein the elongated shaft is configured so that the blood flow path does not pass through the elongated shaft.

17. The kit of claim 16, wherein the elongated shaft comprises a hypotube having a lumen configured to receive a guidewire therethrough.

18. The kit of claim 16, wherein the flexible conduit comprises a distal region and includes a multiplicity of pores configured to permit the blood flow to exit the lumen, the multiplicity of pores comprises at least one of one or more laterally arranged pores or one or more circumferentially arranged pores.

19. The kit of claim 16, wherein the proximal end of the conduit is integrally formed with the outlet of the cannula.

20. The kit of claim 16, wherein the proximal end of the conduit is affixed to the outlet by a stent.

21. The kit of claim 16, further comprising an in-line connector configured to be coupled to the ECMO machine and the cannula, the in-line connector having an inlet configured to be removably coupled to an outlet of an ECMO circuit, an outlet in fluid communication with the inlet and configured to be removably coupled to the inlet of the cannula, and a side arm having a lumen in fluid communication with a lumen of the elongated shaft, the lumens of the side arm and the elongated shaft sized and shaped to receive a guidewire therethrough.

22. A method for improving systemic perfusion, the method comprising:
advancing a distal end of a flexible extension cannula within a patient's vasculature via an elongated shaft coupled to the distal end of the flexible extension cannula such that the flexible extension cannula extends from a location proximal to the patient's renal vessels to a location beyond the patient's renal vessels, a proximal region of the flexible extension cannula coupled to an outlet of an ECMO return cannula in fluid communication with an ECMO machine;
transitioning the flexible extension cannula from a collapsed insertion state to an expanded deployed state when in communication with a blood flow from the ECMO machine, the flexible extension cannula comprising a lumen in the expanded state; and
delivering the blood flow through the lumen of the flexible extension cannula to the location beyond the patient's renal vessels via a plurality of pores disposed at a distal region of the flexible extension cannula to thereby improve systemic perfusion,
wherein the elongated shaft is configured so that the blood flow does not pass through the elongated shaft.

23. The method of claim 22, wherein the ECMO return cannula is coupled to the ECMO machine via an in-line connector comprising an inlet configured to be removably coupled to an outlet of an ECMO circuit, an outlet in fluid communication with the inlet and configured to be removably coupled to the inlet of the cannula, and a side arm having a lumen in fluid communication with a lumen of the elongated shaft.

24. The method of claim 23, wherein advancing the distal end of the flexible extension cannula within the patient's vasculature via the elongated shaft comprises:
advancing a guidewire within the patient's vasculature from the location proximal to the patient's renal vessels to the location beyond the patient's renal vessels; and
advancing the distal end of the flexible extension cannula over the guidewire via the lumen of the elongated shaft until a proximal end of the guidewire extends out of the lumen of the side arm of the in-line connector.

25. The method of claim 24, further comprising removing the guidewire from the patient's vasculature through the lumen of the side arm of the in-line connector.

26. The method of claim 25, further comprising inserting a stylet through the lumen of the side arm of the in-line connector and through at least a portion of the lumen of the elongate shaft to prevent blood flow through the lumen of the elongated shaft during operation of the ECMO machine.

27. The method of claim 22, wherein delivering the blood flow through the lumen of the flexible extension cannula to the location beyond the patient's renal vessels via the plurality of pores reduces left heart workload, reduces myocardial damage, and improves function of mitochondrial CI.

28. The method of claim 22, wherein delivering the blood flow through the lumen of the flexible extension cannula to the location beyond the patient's renal vessels via the plurality of pores ameliorates an effect of compromised lung function and reduces an occurrence and severity of north-south syndrome.

29. The method of claim 22, wherein delivering the blood flow through the lumen of the flexible extension cannula to the location beyond the patient's renal vessels via the plurality of pores reduces myocardial infarct size due to an obstruction of coronary blood flow and limits development of post-infarction heart failure.

30. The method of claim 22, wherein delivering the blood flow through the lumen of the flexible extension cannula to the location beyond the patient's renal vessels via the plurality of pores enhances antegrade blood flow to the patient's descending aorta and adjoining arteries, thereby unloading the patient's left ventricle, reducing cardiac output at a lower pressure, and decreasing left and right ventricular workload.

\* \* \* \* \*